(12) United States Patent
Hagedorn

(10) Patent No.: US 11,529,515 B2
(45) Date of Patent: Dec. 20, 2022

(54) TRANSCRANIAL STIMULATION DEVICE AND METHOD BASED ON ELECTROPHYSIOLOGICAL TESTING

(71) Applicant: Evoke Neuroscience, Inc., Jacksonville, NC (US)

(72) Inventor: David W Hagedorn, Jacksonville, NC (US)

(73) Assignee: Evoke Neuroscience, Inc., Jacksonville, NC (US)

( * ) Notice: Subject to any disclaimer, the term of this patent is extended or adjusted under 35 U.S.C. 154(b) by 0 days.

(21) Appl. No.: 17/675,905

(22) Filed: Feb. 18, 2022

(65) Prior Publication Data

US 2022/0168567 A1    Jun. 2, 2022

Related U.S. Application Data

(63) Continuation of application No. 17/463,606, filed on Sep. 1, 2021, now Pat. No. 11,253,701, which is a
(Continued)

(51) Int. Cl.
| | |
|---|---|
| *A61N 1/00* | (2006.01) |
| *A61N 1/36* | (2006.01) |
| *A61B 5/00* | (2006.01) |
| *A61N 2/00* | (2006.01) |
| *A61N 1/372* | (2006.01) |
| *A61N 2/02* | (2006.01) |
| *A61B 5/291* | (2021.01) |

(Continued)

(52) U.S. Cl.
CPC ........ *A61N 1/36025* (2013.01); *A61B 5/0006* (2013.01); *A61B 5/291* (2021.01); *A61B 5/375* (2021.01); *A61B 5/377* (2021.01); *A61B 5/6803* (2013.01); *A61N 1/36014* (2013.01); *A61N 1/36031* (2017.08); *A61N 1/37247* (2013.01); *A61N 2/006* (2013.01); *A61N 2/02* (2013.01); *A61N 1/0484* (2013.01)

(58) Field of Classification Search
CPC ............ A61N 1/36025; A61N 1/36031; A61N 1/36014; A61N 1/37247; A61N 2/02; A61N 1/0484; A61N 2/006; A61B 5/291; A61B 5/375; A61B 5/377; A61B 5/0006; A61B 5/6803
USPC ................................... 707/600–899; 607/62
See application file for complete search history.

(56) References Cited

U.S. PATENT DOCUMENTS 9,415,222 B2 *   8/2016   DiLorenzo ........... A61N 1/3605

* cited by examiner

*Primary Examiner* — Isaac M Woo
(74) *Attorney, Agent, or Firm* — Woods Rogers Vandeventer Black; Timothy J. Bechen

(57) ABSTRACT

The present method and system provides a neuromodulation therapy including receiving a plurality of input data relating to a patient, the input data including brain value measurements and body value measurements. The method and system includes analyzing the input data in reference to reference data generated based on machine learning operations associated with existing patient data and reference database data. Based thereon, the method and system includes electronically determining, a brain malady and a severity value for the patient and electronically generating a treatment protocol for the patient, the treatment protocol includes transcranial stimulation parameters. Therein, the method and system includes applying a transcranial stimulation using the transcranial stimulation parameters based on the treatment protocol.

19 Claims, 9 Drawing Sheets

Related U.S. Application Data continuation-in-part of application No. 16/914,022, filed on Jun. 26, 2020, which is a continuation of application No. 14/578,764, filed on Dec. 22, 2014, now Pat. No. 10,780,268, which is a continuation of application No. 14/531,012, filed on Nov. 3, 2014, now Pat. No. 8,958,882, which is a continuation-in-part of application No. 14/458,673, filed on Aug. 13, 2014, now Pat. No. 8,938,301, which is a continuation-in-part of application No. 13/742,066, filed on Jan. 15, 2013, now Pat. No. 8,838,247, which is a continuation of application No. 13/543,204, filed on Jul. 6, 2012, now Pat. No. 8,380,316, which is a continuation of application No. 12/979,419, filed on Dec. 28, 2009, now Pat. No. 8,239,030.

(60) Provisional application No. 61/292,791, filed on Jan. 6, 2010.

(51) Int. Cl.
*A61B 5/375* (2021.01)
*A61B 5/377* (2021.01)
*A61N 1/04* (2006.01)

TRANSCRANIAL STIMULATION DEVICE AND METHOD BASED ON ELECTROPHYSIOLOGICAL TESTING

RELATED APPLICATIONS

The present invention is a continuation of U.S. patent application Ser. No. 17/463,606 filed Sep. 1, 2021, issued U.S. Pat. No. 11,253,701, which is a continuation-in-part of claims priority to U.S. patent application Ser. No. 16/914, 022 filed Jun. 26, 2020, which is a continuation of and claims priority to U.S. application Ser. No. 14/578,764 filed Dec. 12, 2014, issued U.S. Pat. No. 10,780,268, which is a continuation of and claims priority to U.S. patent application Ser. No. 14/531,012, filed on Nov. 3, 2014, issued U.S. Pat. No. 8,958,882, which is a continuation-in-part of and claims priority to U.S. patent application Ser. No. 14/458,673, filed on Aug. 13, 2014, issued U.S. Pat. No. 8,938,301, which is a continuation-in-part of and claims priority to U.S. patent application Ser. No. 13/742,066 filed Jan. 15, 2013, issued U.S. Pat. No. 8,838,247, which is a continuation of and claims priority to U.S. patent application Ser. No. 13/543, 204 filed Jul. 6, 2012, issued U.S. Pat. No. 8,380,316, which is a continuation of and claims priority to U.S. patent application Ser. No. 12/979,419 filed on Dec. 28, 2010, issued U.S. Pat. No. 8,239,030, which is based on and claims priority to U.S. Provisional Patent Application Ser. No. 61/292,791 filed Jan. 6, 2010.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD OF INVENTION

The disclosed technology relates generally to the assessment and remediation of abnormal brain and physiological functioning, and more specifically to the utilization of transcranial stimulation and machine learning for brain disease detection and assessment.

BACKGROUND

Traumatic brain injuries can result in physical and/or emotional dysfunction. Post traumatic stress disorder (PTSD) symptoms are similar to those of a mild traumatic brain injury (mTBI) and the two are difficult to differentiate using electrical assessment methodologies such as symptom assessments and questionnaires. In Army deployment, statistics have shown that upwards of 20% of soldiers suffer from mild traumatic brain injury (mTBI). Head and neck injuries, including severe brain trauma, have been reported in one quarter of United States service members who have been evacuated from Iraq and Afghanistan in the first decade of the 21st century A common cause of such injuries arises from exposure to percussive force from explosive devices. Further, recent military analysis indicates that over 90% of patients with acute mTBI will have vestibular (inner ear balance) disorders and those vestibular disorders are present in over 80% of persons with chronic mTBI symptoms. Likewise, stress disorders further affect numerous individuals, whether in a military or civilian situation. Brain injuries may further be incurred from car and bicycle accidents, sports accidents, falls, and the like. Up to 15% of persons suffering even a mild brain injury, or concussion, will suffer from persistent symptoms for more than a year, which significantly negatively affect their ability to work and function in daily life. It is estimated that there are currently 5.3 million Americans living with a disability as a result of a TBI. There are approximately 1.5 million diagnosed brain injuries in the U.S. annually, and it is estimated that another 2 million TBIs occur but are not properly diagnosed. Current assessment methods are either prohibitively expensive or do not diagnose the root cause of the suffering. Thus, there is a need in the art to accurately and quickly assess brain injury and associated dysfunction and then find ways to aid or enhance optimal functioning.

The brain is composed of about 100 billion neurons, more than 100 billion support cells and between 100 and 500 trillion neural connections. Each neuron, support cell and neural connection is extremely delicate, and the neural connections are tiny (approximately 1 micrometer). When the brain moves within the skull, such as occurs in rapid acceleration/deceleration (e.g., exposure to sudden impact and/or explosive devices), axons within the brain can pull, stretch and tear. If there is sufficient injury to the axon or support cells, the cell will die, either immediately or within a few days. Such damage can occur not only in the region that suffered direct trauma but in multiple regions (e.g., diffuse axonal injury). Loss of consciousness is not a prerequisite for mild traumatic brain injury and occurs in less than 5% of mild brain injuries, and head injuries such as diffuse axonal injury are not detectable in routine CT or MRI scan. High false negative findings may lead to patients being undiagnosed or misdiagnosed. Unfortunately current imaging methods still lack the resolution and sensitivity to determine functional brain capacity. Rating scales and other neuropsychological and functional examination methods have long been used to elucidate these functional questions, but they too are fraught with false negative results and limited specificity.

With the high prevalence of age-related cognitive decline conditions, injury from falls, cerebral-vascular events, neurodegenerative conditions (i.e., Alzheimer's Disease) and the many brain injuries occurring in sports and in military operation theaters, there is a need for a rapid and portable assessment instrument that can identify mTBI and neuro-cognitive dysfunction (e.g., balance, processing speed), direct and provide treatment interventions, track recovery progress, and aid in peak performance or the determination of return to leisure activities or duty.

BRIEF DESCRIPTION

The disclosed technology herein provides for electronically determining a brain malady type and a severity value for a patient based on patient input data. For instance, a brain malady may be dementia, depression, brain injury, or any other malady relating to the brain.

The method herein operates in conjunction with a transcranial stimulation device, e.g. headset, and body value measurements, along with machine learning and deep learning operations associating the patient data with reference databases. Therefrom, the method generates a treatment protocol directed to the brain malady type and tailored to the patient.

Yet another object of the disclosed technology is to provide transcranial electrical stimulation (tES) for selective stimulation, based on measures of brain activity and physiological characteristics and measures.

The disclosed technology includes user input and feedback functionality within a clinic or operational settings, whereby user measurements are collected, compared to one or more data sets and adjustments are made to the stimulation output. The data input can include measurement input, as well as clinician input recognizing various patient symptoms, as well as patient information such as lab values, medication information and general patient information. Machine learning/Deep learning (ML/DL) processing techniques are used to analyze the collected data. The ML/DL processing techniques review the data relative to known datasets, performing learning operations, and generate the dementia type and severity values. Based thereon the method and system generates the treatment protocol for the patient, including stimulation modality and scalp location(s). Therefore, the active utilization of the stimulation with additional data allows for application of the stimulation in a controlled environment for improving the efficacy of the stimulation.

In a method of the disclosed technology, electrophysiological data recording and analysis, with manual or automated delivery of tES proceeds as follows. Via at least one electrode and at least one reference and ground electrode and, in one or more embodiments, a plurality of electrodes, non-invasive measurements of electrical currents produced by the brain of a person are conducted, including in one embodiment using a low intensity electromagnetic stimulation. This is done while directed stimuli, such as auditory or visual stimuli or balance tasks (for the purpose of examining brain reactions and processing of stimuli) are administered to the person being tested. A brain functional abnormality in the person, based on the conducting and the measuring, is determined. As a result of analysis of the brain electrical activity at rest and reactions and processing of stimuli, non-invasive brain stimulation using a tES modality of direct or alternating electrical stimulation takes place via said at least one anode electrode and said at least one cathode electrode to said brain of said person.

In embodiments of the above, a single electrode is surrounded by at least three electrodes. When the electrodes are used for stimulation purposes, the surrounding electrodes are of opposite polarity in a cluster. That is, an anode may be surrounded by three cathodes or a cathode may be surrounded three anodes. A plurality of such clusters may be utilized, such as by pre-placement in a form fitting cap or helmet. Each cluster, or any single or plurality of electrodes, may be used to simultaneously or alternately stimulate different regions of the brain, based on the analysis described above.

In a system of embodiments of the disclosed technology, a joint brain electro-analysis and tES system is made up of a plurality of spaced-apart removable and replaceable electrodes arranged in a piece of headgear, an electroencephalography device wired to each of the electrodes, and a transcranial electrical stimulation device wired to each of the electrodes. In this system, upon measuring an electroencephalography anomaly in a brain region with the electroencephalography device, transcranial electrical stimulation is engaged to at least one anode and at least one cathode electrode of the brain region where the anomaly was measured.

An additional device may be used for measuring physiological characteristics of a person wearing the piece of headgear. Such an additional device may measure heart rate variability, balance, cognitive impairment, and/or make pathology comparisons.

Figure 1:
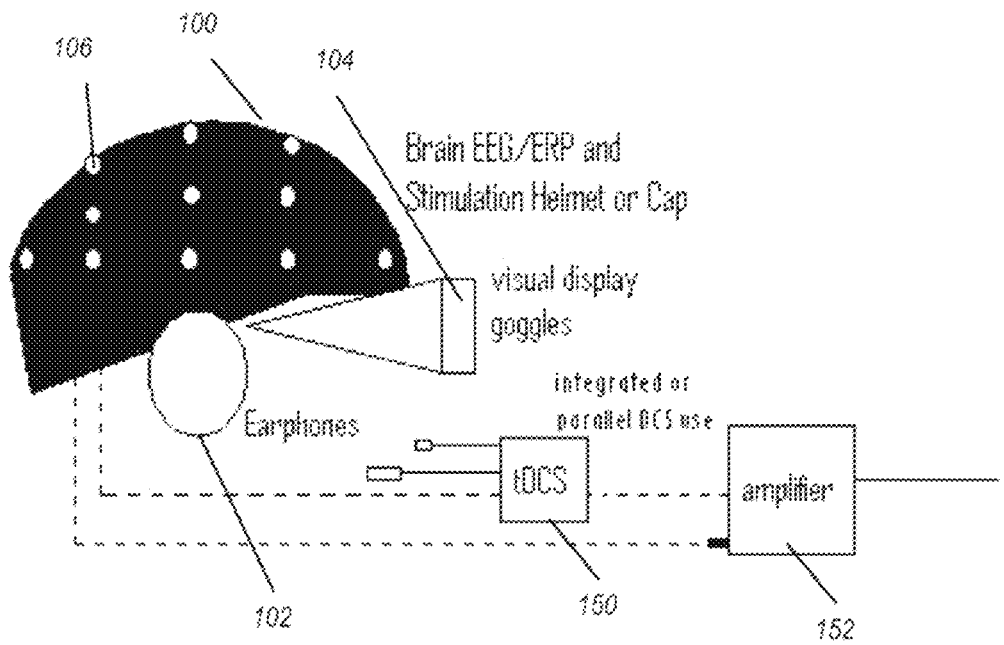
FIG. 1 shows a high level drawing of a device used to carry out embodiments of the disclosed technology.

A better understanding of the disclosed technology will be obtained from the following detailed description of the preferred embodiments taken in conjunction with the drawings and the attached claims.

DETAILED DESCRIPTION

Embodiments of the disclosed technology comprise systems and methods for assessing and repairing neurological pathways damaged by trauma or other brain-related dysfunction, as well as performing assessment and treatment operations in a clinical setting upon multiple users. The collection of data across multiple users may be used for testing or validation of a treatment technique. The methods comprise training a patient and stimulating brain areas where a functional abnormality (such as abnormal electrical activity outside a threshold of voltage, regularity, coherence, phase, and/or rate) has been detected. Such functional abnormalities are determined based on electroencephalography testing, a physiological test that passively monitors electrical current of at least one electrode positioned over the head of a test subject.

Systems of the disclosed technology comprise the use of an electroencephalogram (EEG) which functions by recording electrical activity from the scalp. The EEG measures electrical activity produced by the firing of neurons within the brain. In addition, an event-related potential (ERP) measurement may be used. An ERP, for purposes of this disclosure is a measured brain response that is time locked to a stimulus presented to the subject.

Physiological tests/measurements may be any one of, or a combination of, the following, and are, for purposes of this disclosure, defined as follows: Transcranial electrical stimulation (tES)—application of non-invasive electrical stimulation via at least one electrode which is also usable or used for EEG measurements in embodiments of the disclosed technology. For purposes of this disclosure, non-invasive electrical stimulation also refers to cranial electrotherapy stimulation (CES), which is defined as small pulses of electric current along the head of a subject.

Transcranial magnetic stimulation (TMS) is electromagnetic induction to induce weak electric currents using a rapidly changing magnetic field to cause activity in specific or general parts of the brain, and used for measurement of cortical or distance measures of EEG and EMG for evoked response latency.

Low threshold transcranial magnetic stimulation (lt-TMS) is electromagnetic frequency emitted by way of one or more sensors placed against the scalp to produce a focal field to cause activity in specific or general parts of the brain, and used for neuronal modulation.

Electromyography (EMG) are measurements of electrical potential of muscles.

Computerized neurophysiological testing (NP) is used to estimate a person's peak level of cognitive performance. A person's raw score on a test is compared to a large general population normative sample and/or to the subjects own baseline measurement.

Force platform or balance plate—a stand-on device usable to determine balance and/or vestibular dysfunction. The balance plate can collect and/or record balance and/or postural data, such as the center of pressure and sway movement to analyze vestibular and balance function under different test conditions (e.g., unstable foam pad and eyes closed). The velocity of movement or excursion from balance position can be quantified for comparison to database norms. For some embodiments, the balance plate can be moved without the need for recalibration, for example its use in outdoor settings (e.g., sports, military arena). Collected data can be synchronized by software contained in one or more computers, with visual input stimuli, EEG, ERP and/or other parameters for time-locked variance measures associated with brain dysfunction. For some embodiments, the balance plate may be operated by way of an electrical current connection and instructions carried out by way of a computing device (see FIG. 8) or alternatively with a wireless connection between the plate and the computing device for portable use.

Repetitive transcranial magnetic stimulation (rTMS) includes generating a magnetic field that influences electrical activity in the brain. In rTMS, passing current through a coil of wire generates the magnetic field, the current provided in a repetitive fashion.

Psychological disorder screening—(such as for post-traumatic stress disorder), a component for vestibulo-ocular reflex dysfunction, a component for heart rate variability measures, a component for electroencephalography measures, and/or a component for transcranial magnetic stimulation (TMS) delivery with voltage isolator for simultaneous amplified cortical and distally evoked potential latency measures and motor threshold measures.

By way of the above measurements, while non-invasively monitoring EEG readings of one or multiple sites/regions of the brain, anomalies in neurological impulses are detected. The sites or regions of the brain are then stimulated. As little as one sensor may be used to stimulate, and this anode or cathode may be at the site where the anomaly was detected and may be via the same electrode used to locate the anomaly and which measured the anomalous EEG/ERP measurement. Such an electrode may be in a helmet worn by a user and allows for positive (to increase neural activity) or negative (to decrease neural activity) stimulation at the site where the anomaly was detected.

Such embodiments of the disclosed technology will become clearer in view of the following description of the figures.

FIG. 1 shows a high level drawing of a device used to carry out embodiments of the disclosed technology. A helmet cap 100 comprises at least one, or a plurality of, electrodes 106 (represented as white dots). The helmet may be any receptacle that holds the electrodes in a position relative to the head of a wearer, or alternatively, electrodes may be taped or otherwise placed on the head. Earphones 102, goggles 104 and/or another display device are used in embodiments of the disclosed technology to exhibit stimuli to a user, the stimuli used to vary measurable brain activity. The electrodes 106 are electrically connected to one of an electrical stimulation device 150 or electrical measuring device (e.g., a sensor), such as by way of amplifier 152. The same electrode or electrodes may be disconnected from one such device and connected to another such device, such as by way of changing an electrical pathway (switch) or by physically disconnecting an electrical wire from one device, and plugging into another. In embodiments of the disclosed technology, the electrical stimulation and measuring devices are housed within the same physical device and comprise a switch for changing the electrical pathway, which is manually operated or controlled by pre-programmed instructions. In other embodiments, the measuring device and stimulation device are in separate housings or devices, and only one is electrically connected to the electrode or electrodes 106 at one time. In other embodiments, the electrical stimulation and measuring devices are housed within the same physical devise but have separate outlets to which the electrode(s) may be unplugged and attached. Other devices, not shown, include force platforms (measure postural deviations of person), devices to alter the display on the goggles 104, and devices to alter the sound through the earphones 102, and input devices such as a computer mouse, keyboards, and joysticks.

Referring now to visual stimuli exhibited on a display device, such as the goggles 104 of FIG. 1, the visual stimuli produced may be an "immersive environment," for example a virtual reality 2- or 3-dimension moving "room" displayed through a virtual reality headset. The data collected from the balance plate, heart rate monitor, EEG, and so forth, can be used in conjunction with the visual stimuli for neurophysiological trauma assessment and/or rehabilitation training. The data collected from this component, as well as all other components may be linked with data collected from other components (e.g., EEG, ERP) for assessment purposes.

The system shown in FIG. 1 may further comprise a vestibular activation test (VAT) headset permitting a computerized test that monitors the vestibulo-ocular reflex (VOR) during natural motion. A VAT headset useful for the systems described herein may produce images and/or record eye movements. Images displayed in the VAT headset may be generated by computer-implemented instructions and transmitted via electrical impulses to the VAT headset via wireless or direct connection. Eye movements may be recorded by way of the VAT headset. The VOR is a reflex eye movement that stabilizes images on the retina during head movement by producing an eye movement in the direction opposite to head movement, thus preserving the image on the center of the visual field. As ocular trauma is often concomitant with traumatic brain injury, this component allows additional assessment of injury.

In a clinical or controlled environment, the stimulation techniques described herein are enhanced based on the inclusion of additional data sources and measurements. As described in further detail below, algorithmic processing of multiple data points generate good-fit determinations that trigger individual treatment protocols. Those protocols help define stimulation parameters, such as type of stimulation, location, amount, duration, etc. Moreover, data collection techniques described herein allow for data collection, further processing of the efficacy of the treatment protocol and further adjustments as necessary.

Figure 2:
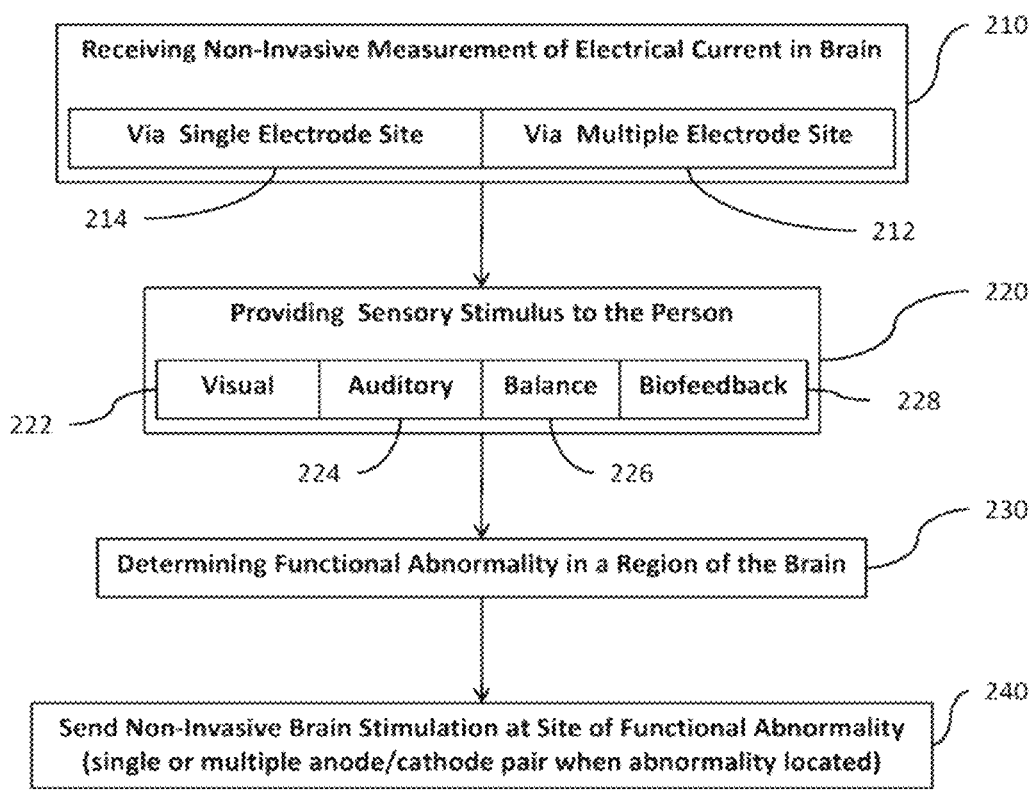
FIG. 2 shows a high level block diagram of a method of carrying out embodiments of the disclosed technology.

FIG. 2 shows a high level block diagram of a method of carrying out embodiments of the disclosed technology. In step 210, non-invasive measurements are made of electrical current in the brain of a test subject. This is accomplished by way of electrodes placed on a test subject, such as in a helmet shown in FIG. 1. In this manner, EEG and ERP signals may be recorded, measured, and analyzed. A single electrode may be used to carry out the measuring in step 214, or a plurality of electrode pairs may be used in step 212. The position of the electrodes is known, and each electrode or a grouping thereof is placed over a definable region of the brain, the region defined by a person carrying out embodiments of the disclosed technology. The region is defined as a specific brain area of interest for the recording, as defined by a person carrying out embodiments of the disclosed technology and may be a region covered by a single electrode pair or as large as half a hemisphere of a brain. Electrodes may also be grouped into clusters, such as with a single anode surrounded by three or more cathodes, or a single cathode surrounded by three or more anodes. Such clusters are electrically connected, such that electric current flows non-invasively through the proximal tissue from anode(s) to cathode(s), stimulating the brain (stimulating, herein is defined as passage of electrical current through the brain and includes increasing or decreasing neuron activity at a site).

While conducting step 210, typically, step 220 is also carried out which comprises providing sensory stimulus to a person. This may be done by way of, for example, the goggles shown in FIG. 1 for a visual stimulation 222, auditory stimulation 224, balance stimulation 226, biofeedback measurements 228, or other sensory stimulations known in the art. Definitions and examples of various types of such stimulations are provided above, before the description of the figures.

Stress tests and peak performance tests may also be performed to determine, for example, how many times a minute a person is able to respond to a stimulus, or how long a person can hold his/her breath or balance on a force platform, etc.

Based on the electrical measurements, that is, EEG or ERP measurements, an abnormality in a region of the brain is determined in step 230. An abnormality may be any of the following: electrical activity which is too infrequent, too frequent, too low in amplitude, too large in amplitude, an improper pattern of electrical activity, inter-intra-hemispheric connectivity, electrical activity in the wrong portion of the brain for the stimulus given, or the like.

In step 240, based on the located functional abnormality, non-invasive brain stimulation (such as tES) is administered at the region of the abnormality. In certain cases, the same electrode which was used to measure the electrical impulses within the brain is used to administer tES or other electrical stimulation. This tES may be low intensity electromagnetic stimulation, such as rTMS and low threshold TMS technology or transcranial sound pulse technology. In this manner, accuracy of the stimulated region may be assured, as there is no difference in the physical location on the head where the existing electrical impulse was measured, versus where the new electrical stimulation is administered. The place of administering may be as little as a single anode/cathode pair (or cluster), or may use multiple anode/cathode pairs (or clusters).

Figure 3:
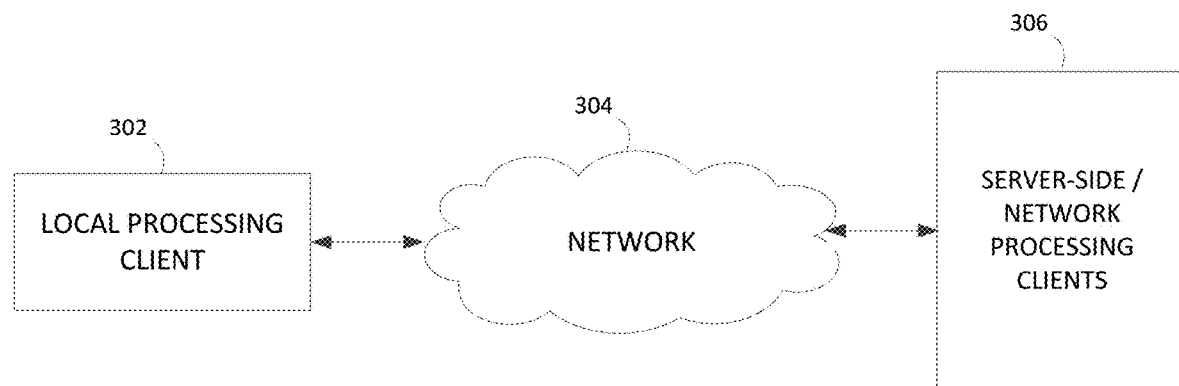
FIG. 3 shows an exemplary processing environment including a cloud or network-based processing client.

Whereby the device of FIG. 1 provides for collection of data, FIG. 3 illustrates an embodiment of processing environment providing for the remote database and data analysis method and system operations. In this system, the local processing client 302 may be any suitable local processing device including but not limited to the collection of measurement data, and/or one or more processing systems for executing interface operations. For example, in one embodiment the local processing client may be a personal computer or a tablet computer having a browser or application for executing the interface functionality described herein.

The network 304 may be any suitable network providing communication thereacross. In one embodiment, the network 302 is an Internet connection across a public access network, wherein it is recognized that the network may include a private and/or secure network, as well as network exchanges via one or more service providers. The network 304 operates to facilitate the communication of data between the local processing client 302 and the server-side network processing clients 306.

The server-side network processing clients 306 may be any suitable number of network-processing devices. In one embodiment, the client 306 may be a dedicated processing server, wherein in another embodiment, the client 306 may be any suitable number of distributed computer resources for processing operations as described herein.

Tests are used to measure psychological characteristics of a test subject. The purpose of at least some of these tests is to assess the ability of the test subject to automatically and fluently perform relatively easy or over-learned cognitive tasks relevant to the ability to process information automatically or rapidly and measure executive function complex decision-making capacity. Test can be performed on one or more suitable devices, such as a processing device providing a display. Such tests include, but are not limited to, trails making test, grooved pegboard, symbol-digit test, digit coding, symbol search, Stroop test, finger-tapping tests, categories test, Wonderlic tests and Wechsler subtests, Wisconsin Card Sort Test, matrix reasoning, Raven Progressive Matrices tests, and/or components of the neuropsychological assessment batteries. Still another type of test is a test of malingering (e.g., TOMM) which can be part of a comprehensive assessment of both mTBI (mild traumatic brain injury) and PTSD, as such tests aid in determining actual impairment resulting from neurophysiologic impairment as opposed to subject feigning or exaggerating. Such tests can assist in minimizing false positive mTBI diagnoses. Psychological questionnaires, for example a set of questions designed to diagnose a particular psychological disorder, such as PTSD, can also be included in computerized or hard copy form.

An additional component, a single pulse (0.9-1.5 tesla) fixed or variable Hz setting transcranial magnetic stimulation (TMS) device may be linked to a voltage isolator with linked amplifier for synchronized EEG, ERP and/or electromyogram (EMG) recordings or low threshold magnetic stimulation (lt-TMS) that operates independent of a voltage isolator. The amplifier (such as amplifier 152 of FIG. 1) may be a multichannel amplifier for multiple modality physiological measurements (e.g., EMG, ERP, EEG, temperature, blood volume pulse, respiration, skin conductance, EKG, blood pressure, etc.). Sensors for each physiological measurement may also be connected to the amplifier, for example as a means to collect measurements from a test subject. TMS and transcranial soundwave pulse stimulation are non-invasive techniques utilizing magnetic fields to create electric currents in discrete brain regions. Typically, during TMS, a time-pulsed magnetic field is focused on cortical tissue via a coil placed near the area to be affected (e.g., M 1, Dorsolateral Prefrontal Cortex (DLPFC)). TMS can be utilized for various measurements of intracortical inhibition and facilitation, for example short interval intracortical inhibition (SICI), long interval intracortical inhibition (LICI) and contralateral cortical silent period (CSP). Such measurements can aid in differential diagnosis between individuals with mTBI and mTBI with PTSD. Any commercially available TMS device known in the art may be utilized. For some embodiments, the TMS device utilized is portable.

Low intensity electromagnetic stimulation has been shown to have certain and safe clinical value, with rTMS technology being one example. Low threshold stimulation below that of rTMS available in this device is called low threshold transcranial magnetic stimulation (lt-TMS). This electromagnetic stimulation is one of the methods utilized in this device yet with the added benefit of being able to apply such stimulation to one or more location points on the scalp within a given session or predesigned treatment sequence to stimulate along a neuronal network rather than one location along that network.

The lt-TMS is delivered using either a pulsed (or pulse-train) or sinusoidal electromagnetic stimulation waveform and is delivered based on the manual operation of the device or programed delivery based on deviation measures from a normative or comparison database of collected EEG and ERPs produced by the same device. The device is designed to record electrophysiology allowing for a pre and post measure of such electrophysiology when utilizing any of the stimulation types within the device (tDCS, tACS, tRNS, lt-TMS).

While rTMS has limitations of stimulation rate below 20-30 Hz due to heat, the selection of lt-TMS within the device allows for longer session durations and faster stimulation.

In one embodiment, lt-TMS delivery can be performed manually at either one or multiple locations. Delivery at multiple locations can be done simultaneously or in timed preselected or preprogrammed sequence of locations. Another benefit of lt-TMS is the real time measuring of the electrophysiology before and after stimulation. The electrophysiology can also be measured as part of a preprogrammed stimulation sequence. Furthermore, lt-TMS electromagnetic stimulation permits longer stimulation durations without heating the neuronal tissue and with a larger range of frequency selections 0.1-100,000 Hz.

Figure 4:
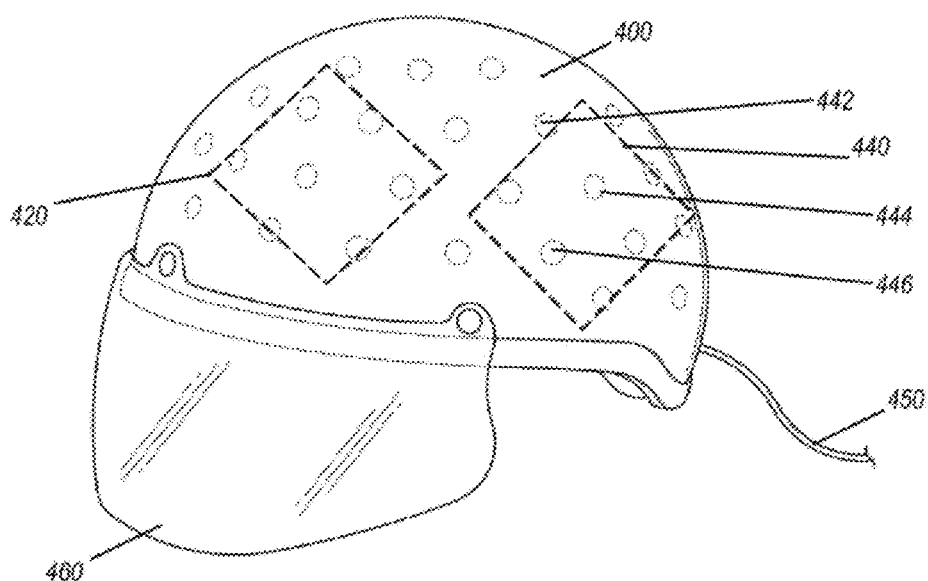
FIG. 4 shows a perspective view of a helmet with electrodes used in embodiments of the disclosed technology.
Figure 5:
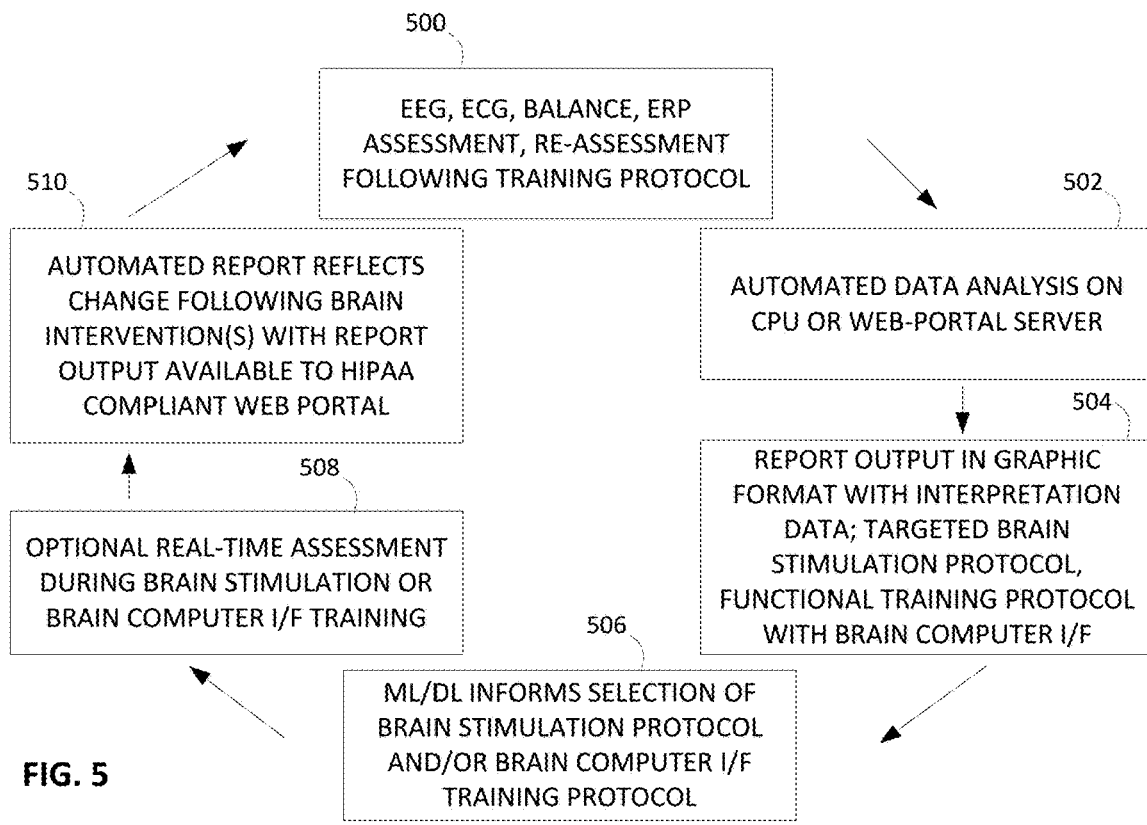
FIG. 5 illustrates one embodiment of a flow diagram for data analysis.

FIG. 4 shows a perspective view of a helmet with electrodes used in embodiments of the disclosed technology. FIG. 5 shows a bottom view of such a helmet. The helmet 400 comprises multiple electrodes, such as electrodes 442, 444, and 446. As can be seen in the figure, a plurality of electrodes are spaced apart around the interior of a helmet or other piece of headgear and are adapted for both reading electrical activity from the brain of the wearer and delivering new impulses. That is, by way of a single electrode, plurality thereof, cluster of electrodes, or plurality of clusters, a joint brain electro-analysis and transcranial electrical stimulation system (tES) comprises a plurality of spaced-apart removable and replaceable electrodes arranged in an item of headgear. An electroencephalography device (such as an EEG) is wired to each of the electrodes, as is a transcranial electrical stimulation device (at the same time or alternating by way of a switch or plugging/unplugging a cable between the devices). In one embodiment, using lt-TMS, the stimulation sensors are smaller than conventionally larger (25-35 cm2) in order to provide both a quality electrophysiology measure and to deliver a more focal stimulation.

Due to the know dielectric properties of skull and scalp tissue the device permits a dose-response adjustment such that the user can adjust frequency and intensity according to measured electrophysiology changes taken at the stimulation location or all scalp locations (e.g., EEG amplitude, EEG coherence, ERP amplitude and latency) and accordingly adjust stimulation thresholds to a level of desired neuronal tissue modulation.

A cable 450, which will be discussed at greater length with reference to FIG. 6, allows for electrical connectivity between the electrodes and either or both of a tES and EEG device. Further, a visor 460 is integrated with the helmet in embodiments of the disclosed technology for optical stimulation (e.g. a video monitor). The device cap/helmet is constructed with an optional extension cable and materials such that simultaneous magnetic resonance imaging can occur while the device is in use.

Upon measuring an electroencephalography anomaly in a brain region with the electroencephalography device, transcranial electrical stimulation is engaged to at least one anode and at least one cathode electrode to the brain region where said anomaly was measured. Additional devices, as disclosed above, such as a force plate, visual stimuli utilizing interactive games and tests, and the like, may also be utilized. The transcranial electrical stimulation device, in embodiments of the disclosed technology, is engaged only when either a) data from the electroencephalography device indicates that electrical impulses in the brain are outside a predefined range/threshold of where they should be or where is desired by the administrator of the device; and/or b) when the additional physiological characteristic, as measured with another device disclosed in the specification herein (such as an EMG device, balance plate, pathological test, etc.) is out of range of a predefined allowable threshold. Thus, the ability to administer tDCS may be limited by the above factors and, as a safety measure, may be further limited automatically by way of pre-programmed instructions in a computer device (see FIG. 8) or manually by way of a physician or other clinical practitioner relying on such data.

The device delivers subthreshold polarization that potentially causes polarization at the soma and thereby obtains deeper brain source penetration and delivers a greater effect with a least intrusive and in a safer manner than high intensity stimulation. The device permits a programming of stimulation type (tDCS, tACS, tRNS, lt-TMS) delivery interrupted by electrophysiology measures (e.g., EEG, ERPs) in order to ascertain the relative difference each stimulation type has on neuronal activation or suppression such that the most efficient and effective intervention can be then applied for the individual.

Referring further to a force plate (which includes a "balance plate" in embodiments of the disclosed technology), the device is used as follows. The force plate collects (and may record) balance and/or postural data, such as center of pressure, sway movement, and movement velocity to analyze vestibular and balance function under different test conditions (e.g., unstable foam pad and eyes closed). For some embodiments, the balance plate may be moved without the need for recalibration, for example use in outdoor settings (e.g., sports, military arena). Collected data may be synchronized with visual input stimuli, EEG, ERP and/or other parameters for time locked variance measures associate with brain dysfunction. In some instances, visual stimuli are provided to a subject while the subject utilizes the force plate. The visual stimuli produced may be an "immersive environment", for example a virtual reality 2- or 3-dimension moving "room" displayed through a virtual reality headset. The data collected from the force plate is used, in embodiments of the disclosed technology, for neurophysiological trauma assessment and/or rehabilitation training.

As further seen in FIG. 4, the anodes and cathodes may be in a cluster 420 and 440. The clusters shown are by way of example. That is, one anode (e.g., 444) may be surrounded by three or more cathodes (e.g., 442, 446, and others), or one cathode may be surrounded by three or more anodes. Anodes and cathodes have opposite polarity, and where neural activity is too high in a region, a cathode may be used to suppress activity. Where neural activity is too low in a region, an anode may be used to increase activity. This may be done between two electrodes, a cluster, or a plurality of clusters. In two different regions, it may be desired, in embodiments of the disclosed technology, to stimulate (or de-stimulate) simultaneously. In this context, "simultaneously" may be defined as being at the same time or alternating. Different rates of stimulation at each region may also be used, as necessary. That is, two regions that should not be linked, in fact are. By firing at different times or rates, in different regions (at the second region, firing from 0 to 180 degrees off, in a phase between two firings of the first electrode), two synced regions may be brought out of phase. This may normalize brain activity as regions of the brain require specific phase similarities and differences depending upon their relative function. Similarly, by firing at the same time, two out of sync regions may be brought in phase. Now, the two regions are said to have coherence. Biofeedback (a user viewing his/her own EKG, EEG, ERP, or other indicators of physiology function) may be utilized in conjunction with the tDCS, so as to give the user the ability to consciously control his or her brain or other physiological activity to help the healing process when attempting to normalize brain or physiological function (e.g., heart rate variability) activity.

The electrodes may be separable, so as to be individually placed, or may be within a sized EEG cap or helmet (such as helmet 100 of FIG. 1). The electrodes, which can also be used as anodes and cathodes for purposes of tDCS, may be directly connected to one or more stimulation devices (e.g., tDCS or CES stimulation) and/or measuring devices (e.g., EEG recording device) simultaneously, or via a switch or removable plug to switch between such devices. When measuring EEG/ERP readings (electrical impulses from the brain of a user), various activities (stimuli or physiological measurements) may take place simultaneously. A finger depression device may be used, and others such as a force platform, heart rate monitor, EMG (muscle electric potential), interactive biofeedback devices allowing the user to monitor internal activity (directly or by way of a game used to control by way of biofeedback), and the like. These measurements may then be compared against a database of known human population normative values as indications to determine a deviation from normal function, check the deviation against what is being monitored by way of EEG measures and abnormalities of electric impulses in the brain, and in some embodiments, a correlation may be made to determine brain abnormalities associated with different dysfunctions. In other embodiments, the brain abnormalities will serve to verify a particular dysfunction. In still further embodiments, based on prior determined data of brain electrical abnormalities for a specific pathology, tDCS or other electrical stimuli (e.g., CES) is then induced at a region where the brain abnormality is measured.

For example, a database may contain reference EEG components for normal and known pathological results (e.g., IED blast brain trauma, motor vehicle accident brain trauma, Attention Deficit Disorder, Alzheimer's disease). In some instances a database may comprise subcategorization of data from collected EEG and ERP data. Comparison of subject EEG and ERP results to such databases can allow for EEG and ERP analysis as part of the diagnostic process. Source localization methods (to determine specific regions of interest and dysfunction) may be accessed for selected EEG and ERP components.

When transcranial electrical stimulation (tES) is used as a result of the above measures, the current may be via the EEG electrodes or can be delivered by other anode and cathode electrodes (i.e., anode sensors or cathode sensors placed from a different system) designated for tES treatment. For example, sponges may be attached to graphite composite sensor pads sized for anode and/or cathode to ensure proper contact with the subject. The tES device, in embodiments of the disclosed technology, directs anodal or cathodal non-invasive brain stimulation to one or more of the connected site locations on the subject. Stimulation can be delivered as transcranial current, or other effective current type, in amounts between about 0.25 mA and 6.0 mA.

Upon measuring an electroencephalography anomaly in a brain region with the electroencephalography device, transcranial direct electrical stimulation is engaged to at least one anode and at least one cathode electrode to the brain region where said anomaly was measured. Additional devices such as a force plate, visual stimuli utilizing interactive games and tests, and the like, may also be utilized.

As used herein, the tES may include, but is not expressly limited to, transcranial direct current stimulation (tDCS) or transcranial alternating current stimulation (tACS). The data collection techniques and operations, as described in U.S. Pat. Nos. 8,239,030; 8,380,316; and 8,838,247 are herein incorporated by reference.

The data is collected and thus provided to one or more remote data processing systems. These remote data processing systems may be connected via a networked connection, including in one embodiment an Internet-based connection. In additional embodiments, the networking may be via a private or secure network. Wherein, it is noted that Internet-based connections include the processing of security features with the data, to insure the privacy of the data during transmission.

For example, one embodiment may include a data collection computing device, such as a personal computer or other type of processing device, operative to receive the electrophysiology data. The processing device therein provides for the encryption or inclusion of security features on the data and the transmission to one or more designated locations. For example, one embodiment may include the compression of the data into a ".zip" file.

The server further provides for the storage of the data and retention of data information. In this embodiment, the server creates a postscript formatted file, such as a PDF file and the database is then updated to include storage of this information. In one embodiment the database further includes enhancements to maximize storage, including determining if the data to be stored is duplicative. If the data is duplicative, a single data link can be provided, but if the data is not duplicative, then separate access to the data is provided.

The data acquired from the device may be processed locally or across network. In a typical embodiment, the user or client is a doctor or other medical specialist having the ability to review, understand and advise a patient based on the data generated in the reports. As noted above, the data generated in the reports relate to the electrophysiology data acquired from patients.

The complete system consists of a wireless amplifier equipped to record artifact free electrical signals from the brain and heart and also position in space using a nine or greater accelerometer. This same device is configured to deliver electric current back to the sensors that are in contact with the scalp in order to facilitated non-invasive brain stimulation. Sensors make contact with this skin using either dry sensors or electro dermal gel or saline impregnated sensor for consistent sensor to skin connectivity measured by impedance.

The software provides for automated data collection using script software and self-guided instructions. The software sends the resulting data for algorithm processing either on the CPU or on a dedicated secure server through an internet connection. This data is processed on the CPU and processed either on the installed database and processing software or transmitted to the cloud-based server where processing takes place.

The data analysis is returned in a report format showing physiology graphics and interpretive results from which the user can make intervention or diagnostic decisions. Several comparison databases can be selected from within the software to provide a comparison measure for the data analysis. Pre-set EEG training protocols (e.g., theta:beta ratio training for attention; alpha:theta ratio training for relaxation) are configured for automated home or clinic based training.

Individual baseline data can also be utilized so that the individual's data can be compared to an earlier data sample. An example of this is a professional athlete having his or her pre-season baseline that is used for comparison following a concussion. This is particularly useful for single-subject design research of change over time and intervention results. Group databases such as peak performance or pathology comparison databases (i.e., Alzheimer's disease sample database) are also available for selection and data comparison. Intervention options include real-time noise and artifact removal algorithms that permit EEG and ECG training devoid of movement and other disruptive artifact or signal noise. Individual differences from the selected comparison database permits specific or individually derived interventions as non-invasive brain stimulation (e.g., tDCS/tACS) and brain computer interface (sLORETA/eLORETA brain computer interface, wavelet time-frequency neurofeedback, event-related potential neurofeedback; Brodmann Area selection, neurofeedback, neuro-network brain computer interface) and peripheral biofeedback such as heart rate variability biofeedback).

The brain computer interface or neurofeedback can include any number of operations or techniques, including for example low resolution brain electromagnetic topography source localization feedback and surface electroencephalography amplitude or phase or coherence feedback.

The user receives report and intervention information from cloud-based server interface or from optional embedded software on the CPU for usage where internet connectivity is not possible.

The results of the data analysis include a protocol that directs the non-invasive brain stimulation sensor placements and current parameters. These stimulation protocols can be manually or automatically selected to provide the user with both brain compute interface training and brain stimulation or brain modulation interventions.

The rapid assessment and re-assessment of the brain and other measures included in the physiology measurement battery allows for rapid determination of brain computer interface training location and frequency protocols and also brain stimulation or modulation using electric current. The re-assessment quantifies the difference from the baseline measure in order to generate a report showing the change made by either or both brain computer interface and electric current brain modulation.

The re-assessment then provides an updated intervention protocol. Protocols will vary based on the assessment results such that the different locations on the scalp may be stimulated with different polarity at the sensor and with more or less milliamps than one another. Users can manually define scalp location, polarity at the sensor, and milliamp levels and duration at each location. Users can also select from pre-defined protocols to increase or decrease regional neuronal activity.

The same data analysis report provides illustration and instruction on the current flow through the brain tissue in order to further quantify the cortical excitability relevant to the users clinical or performance intent. Current flow reporting aid the user with further and more specific brain modulation targeting protocols using Talairach or other available coordinate source location libraries and Brodmann Areas. The availability of the data analysis and reports on the web portal allows for telemedicine access and review.

The sensors permit real time stimulation with electrical current and simultaneous recording of EEG using signal filters that remove the electrical stimulation and permit only the EEG and event related potentials to be recorded and processed. This feature permits the user to combine targeted brain stimulation with brain computer interface training using real time artifact correction. Simultaneous neurofeedback with stimulation allows for data analysis showing the focal changes or modulation in the brain from the individual or combined intervention modalities.

FIG. 5 illustrates a circular data flow diagram representing the circular operations described herein. Step 500 includes the assessment and re-assessment protocols, such as EEG, ECG, Balance, ERP, etc. Step 502 is the automated data analysis on a CPU or networked server. Step 504 is the report output, which may include output in graphical format with interpretation data. The report 504 may further include targeted brain stimulation protocol, functional training protocol with brain computer interface.

Continuing in the cycle of FIG. 5, step 506 is the automated or manual selection of brain stimulation protocol and/or brain computer interface training protocol. Step 508 is an optional real-time assessment during brain stimulation or brain computer interface training. Step 510 provides automated reporting that reflects changes following brain intervention(s) with report output, which can be available to a user including HIPAA-compliant web or network portals.

Figure 6:
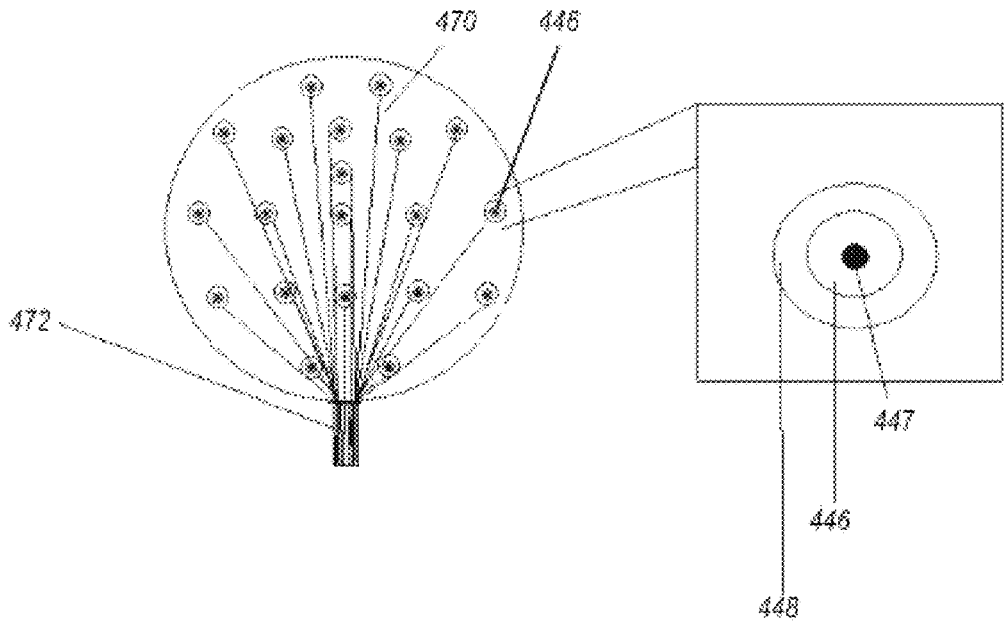
FIG. 6 shows electrical pathways to electrodes within a helmet of an embodiment of the disclosed technology.

FIG. 6 shows electrical pathways to electrodes within a helmet of an embodiment of the disclosed technology. Electrical connections (such as connection 470) provide an electrical pathway to and from each electrode and join at a cable 472 housing all electrical connectors between each electrode and an amplifier or other equipment for sending and/or receiving electrical impulses. Each electrode, such as electrode 446 comprises the electrode itself (typically, a metal or other known conductor, the conductor being removable from an electrode housing 448 with disposable electrode boot 449 in embodiments of the disclosed technology) with a hole 447 for inserting conductive gel.

Figure 7:
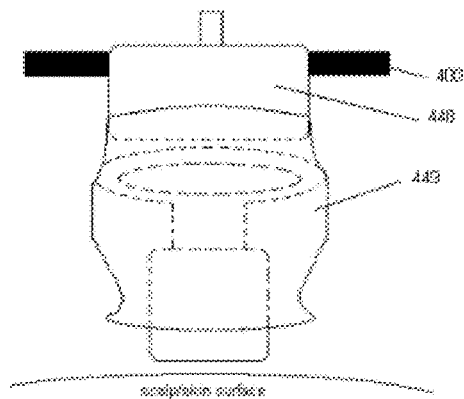
FIG. 7 is a side view of an electrode with disposable electrode boot attachment used in an embodiment of the disclosed technology.

FIG. 7 is a side view of an electrode with disposable electrode boot used in an embodiment of the disclosed technology. An encasement 448, such as one made of hard plastic covers the electrode. The electrode 449 is attached within the helmet 400. A disposable foam conductive patch is inserted, in embodiments of the disclosed technology, into an electrode sensor. Conductive gel permits a conductive connection from the electrode, and by extension the foam patch insert, to the skin. This connection permits both the recording of cortical electrical activity and the delivery of anodal or cathodal direct current. Two version of this electrode are available: (1) the first version is a soft rubber boot that can be wrapped around a hard plastic electrocap device. This soft boot slips onto any of the electrocap sensors and has within it a porous foam or sponge pad. The connective gel that is inserted into the electrocap hole also flows into this boot as shown in the art. (2) A second version is a harder plastic, carbon, or graphite material replacement sensor that connects to any wire harness for EEG/ERP and may be built into a helmet or softer cap.

In an embodiment of the disclosed technology, a single interface is used to control EEG, ERP, and tES and is electrically or wirelessly connected/engaged with any one of or a plurality of inputs including ECG sensors, a balance plate, a headset, a tES cap, or the like. Between the input devices and the interface may be a voltage isolator and/or amplifier. The interface, or a separate computational device may be used for data collection and analysis from the EEG/ERP cap and other inputs. Visual images may be displayed on a headset and visual and auditory stimuli may be provided by way of a monitor and speakers, respectively.

Figure 8:
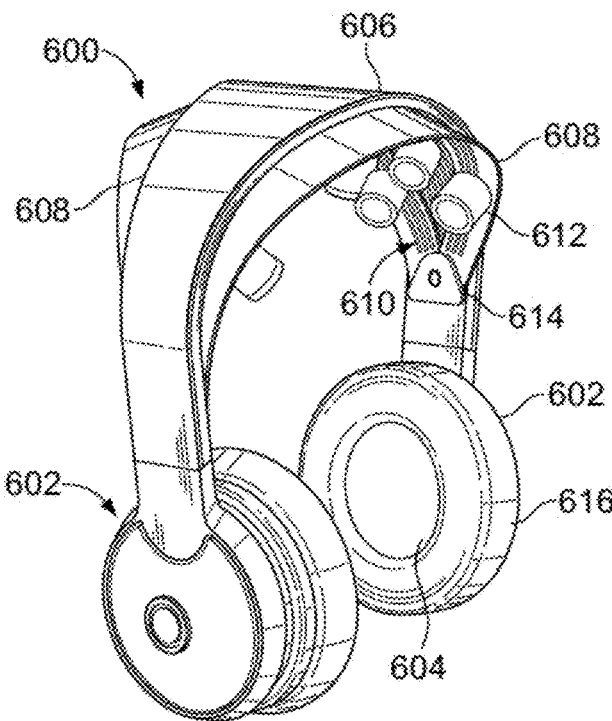
FIG. 8 illustrates another embodiment of a headgear.

FIG. 8 illustrates another embodiment of a device for collecting data and providing user feedback. This device 600 includes earpieces 602 with speakers 604. The device 600 further includes a top cross-bar 606 and side-bars 608, the bars, 606 and 608, having a track 610 thereacross with sensors 612 disposed therein. The device 600 additionally includes a hinge 614 for the side-bars 608. Further embodiments include an articulating arm 618 having a lens 620 thereon.

The headgear 600 may be composed of one or more suitable materials, including plastic, metal or carbon fiber by way of example. The earpieces 602 are representative embodiments of engagement portions providing for engaging the user's head and securing placement of the sensors 612. In the illustrated embodiment of FIG. 6, the speakers 604 are disposed within the engagement portions of the earpieces 602, providing for the audio output of sound consistent with known speaker technology. In this embodiment, the earpiece 602 and speaker 604 include cushioning 616 that not only improves user comfort in wearing the device, but also improves sound isolation of the speaker to minimize or reduce any ambient noise.

The cross bar 606 and side bars 608 include the track 610 that allows for the insertion of the sensors 612. The sensors 612 may be any suitable sensors that connect into the track for electrical connection with the device 600. In one embodiment, the sensors 612 are dry sensors, where the dry sensors are attached using magnets for easy removal and replacement in-between users and for alternate sensor or electrode type attachments. The same system both provides EEG/ERP measures but also delivers brain stimulation using direct current and/or alternating current, as described above.

When worn by a user, the sensors 612 are in contact with the user's cranium, wherein the location of the sensors 612 can be adjusted by movement of the sensor 612 along the track 610 within the cross-bars 606 and 608.

The hinge 612, disposed on both sides of the cross-bar 606, allows for the articulation of the of the side bars 608 away from or towards the cross-bar 608. Therefore, when worn by the user, the sensor 612 location of the user's cranium can also be adjusted by the inward or outward articulation of the side bars 608.

In embodiments including the arm 618 and the lens 620, the headgear 600 allows for the visual display of content on a lens, not expressly shown. The positions or location of the lens relative the user can be adjusted by the adjustment of the arm 618. The arm 618 includes wiring (not readily visible) for providing an output signal to the lens. In one embodiment, the lens may be a high-definition lens operative to provide a visual output viewable by the user, where as described herein, the user can be subjected to visual stimuli for feedback generation via the headgear. In this embodiment, the lens operates similar to the visual display goggles 104 of FIG. 1 or the visor 460 of FIG. 4.

The above data collection and stimulation operations provide for clinical operations for improving and optimizing neurostimulation functionality. As used herein, a clinical operation is not expressly limited to a clinic, such a medical or rehabilitation clinic, but can additionally include an location wherein the use of the operations described herein are performed.

Moreover, the described methodology is functionally operational based on one or more processing devices operating in conjunction with one or more databases as well as a neurostimulation device as described herein.

Figure 9:
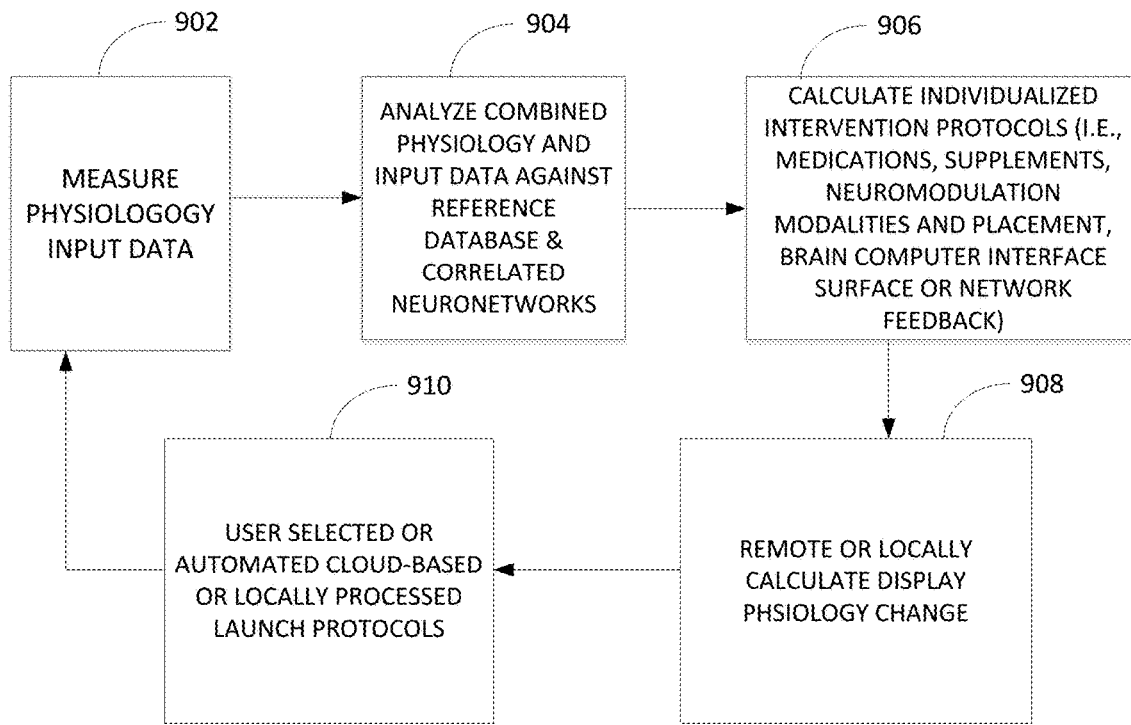
FIG. 9 illustrates a data flow diagram illustrating an overview of one embodiment of a clinical application process.

FIG. 9 illustrates a generalized flowchart of one embodiment of the clinical application for neurostimulation. The methodology is quantified into five categories, a data collection phase, a data analysis phase, an intervention selection phase, an invention delivery phase, and a change analysis. The phases noted in FIG. 9 are described in greater detail in FIGS. 11-15 below.

The methodology of the phases are performed using processing devices for computations, accessing databases for the acquisition of various data sets, measuring and testing devices for the acquisition of patient information, as well as computing interface(s) for data collection, e.g. patient questionnaire, as well as the utilization of the herein described neuromodulation device for application of stimulation to the patient.

Phase 902 is the receipt of input of the measured physiology data. Phase 904 is the analysis of combined physiology and input data against reference database and correlated neuronetworks. Phase 906 is the calculation of individualized intervention protocols. Such protocols may include, but are not expressly limited to, medications, supplements, neuromodulation modalities and placement, brain computer interface surface network or network feedback. Phase 908 is the display of physiology change, calculated either locally or remotely. Phase 910 is the user selection or automated network-based or locally processed launch protocols. In one embodiment, the methodology is iterative, wherein step 902 is therein repeated.

Figure 10:
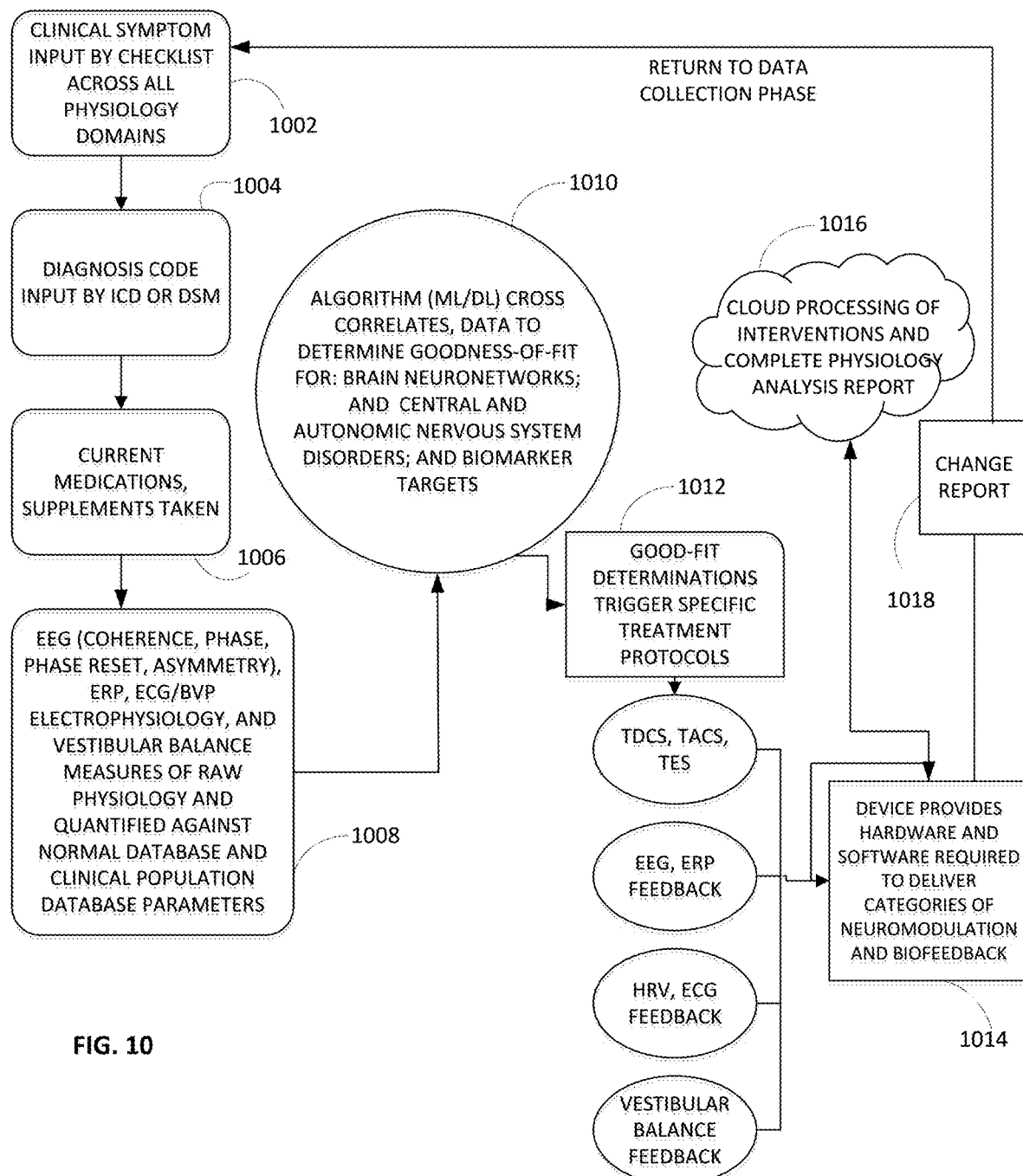
FIG. 10 illustrates a phase-based flow diagram of one embodiment of a clinical application process.

FIG. 10 illustrates another flow diagram of multiple embodiments of the clinical use application described herein. While iterative in nature, the first illustrated step, step 1002 is the receipt of clinical symptoms based on checklists across physiology domains. Step 1004 is receipt of diagnosis code by ICD or DSM. Step 1006 is receipt of current medications and any supplements taken by a patient. Step 1008 include receipt of measurement data, such as but not limited to EEG, ERP, ECG/BVP Electrophysiology, and Vestibular Balance measures of raw physiology and quantified data against normal database and clinical population database parameters.

In step 1010, the methodology provides for cross correlation of data to determine good of fit for: brain neuronetworks; and central and autonomic nervous system disorders; and biomarker targets. This step may be performed based on one or more processing devices accessing one or more databases having data sets therein.

Step 1012 provides that good-fit determinations trigger specific treatment protocols, such as the exemplary list of protocols for neuromodulation and biofeedback in FIG. 10.

Step 1014 includes one or more processing devices providing hardware and software required to deliver the neuromodulation and biofeedback from the various protocols. In another embodiment, or in addition to step 1014, step 1016 provides for cloud-based or network-based processing of interventions and complete physiology analysis report.

Step 1016, provides for a change report. This report indicates adjustments to the neuromodulation and biofeedback. Thereupon, the clinical operations revert back to a data collection phase of collection data about the patient to further iterate the treatments using neuromodulation and biofeedback.

Figure 11:
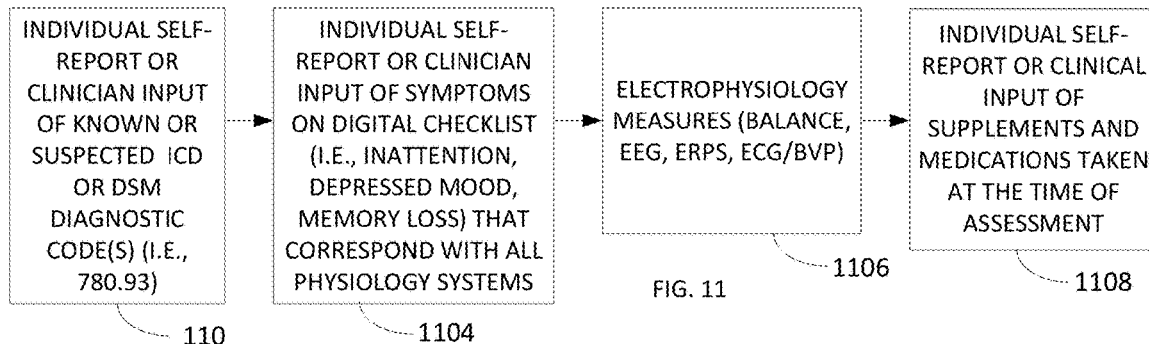
FIG. 11 illustrates a data flow diagram of one embodiment of a measured physiology plus input data phase of the clinical application process.

FIG. 11 illustrates one embodiment of the acquisition of data relating to the patient, including measured physiology and other input data. Step 1102 is the receipt of individual self-reporting or clinician-input of known or suspected information. One embodiment may include the inclusion of ICD or DSM diagnostic codes. This data may be received via any suitable data processing interface, including via data entry a user interface, accessing a patient database, or any other suitable means.

Step 1104 is the receipt of the input of symptoms. One embodiment may include selection or recognition on a digital checklist. Symptoms, by way of example, may include lack of attention to detail, depressed mood, aphasia, memory loss, among others. The input of step 1104 may include input to any or all physiology systems of the patient.

Step 1106 is the receipt of electrophysiology measures. Exemplary measures include balance, EEG, ERP, ECG/BVP. Wherein receipt of these measures may be acquired, in one embodiment, using the techniques described above, including techniques relating to FIGS. 1-7.

Step 1108 is the receipt of individual or self-reporting or clinical input of supplements or medications taken at the time of assessment. Similar to step 1104, this input may be via any suitable interface including data entry or in another embodiment accessing a related database having the data therein.

The input of data may include additional data, wherein the steps 1102-1108 are exemplary and not limiting in nature. Thereupon, in one embodiment, the first phase (phase 902 of FIG. 9) is completed based on the collection of data described herein.

Figure 12:
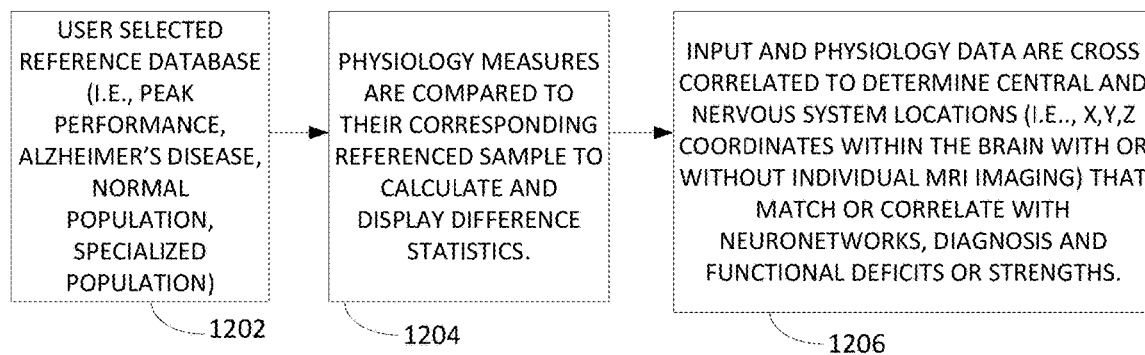
FIG. 12 illustrates a data flow diagram of one embodiment of an analysis-combined physiology and input data phase of the clinical application process.

FIG. 12 illustrates steps relating the second phase, phase 904 of FIG. 9. This phase relates to the analysis of data based on reference data. Not expressly illustrated herein, the methodology includes access to one or more databases having the referenced data therein. The reference database(s) may be locally or remotely stored, wherein access may be using recognized database accessing protocol(s).

Step 1202 is accessing the user selected reference database. This database may be selected in reference to an underlying or anticipated condition of the patient. The database may be selected based on requested reference data for further processing of the input data. For example, the reference database may include peak performance data, Alzheimer's data, normal population data, specialized population data, etc.

Step 1204 provides for comparing physiology measure to corresponding referenced sample data as may be acquired in step 1202. The comparing in step 1204 provides for calculating and displaying differences in the data sets, in one embodiment.

Whereupon, in step 1206, input and physiology data are cross correlated to determine central and nervous system locations (i.e. x, y, and z coordinates within the brain with or without individual MRI imaging) that match or correlate with neuronetworks, diagnosis and functional deficits or strengths. Thereupon, in one embodiment, step 1206 generates generalized location information for the application of neurostimulation based on the data calculations described herein.

Scalp electrical potentials are recorded from the surface placed electrode sensors and solutions (eLORETA, sLORETA) to the inverse problem are used to source intracranial signals for using more than one method of localization. One example of this method to compute cortical current density with optimized localization capacity and dynamic functional connectivity in the brain is by the use of eLORETA published by Roberto D. Pascual-Marqui. Reference: Pascual-Marqui. RD, Lehmann, D, Koukkou, K, et al. (2011). Assessing interactions in the brain with exact low-resolution electromagnetic tomography. *Philosophical Transactions of the Royal Society A,* 369, 3768-3784.

Figure 13:
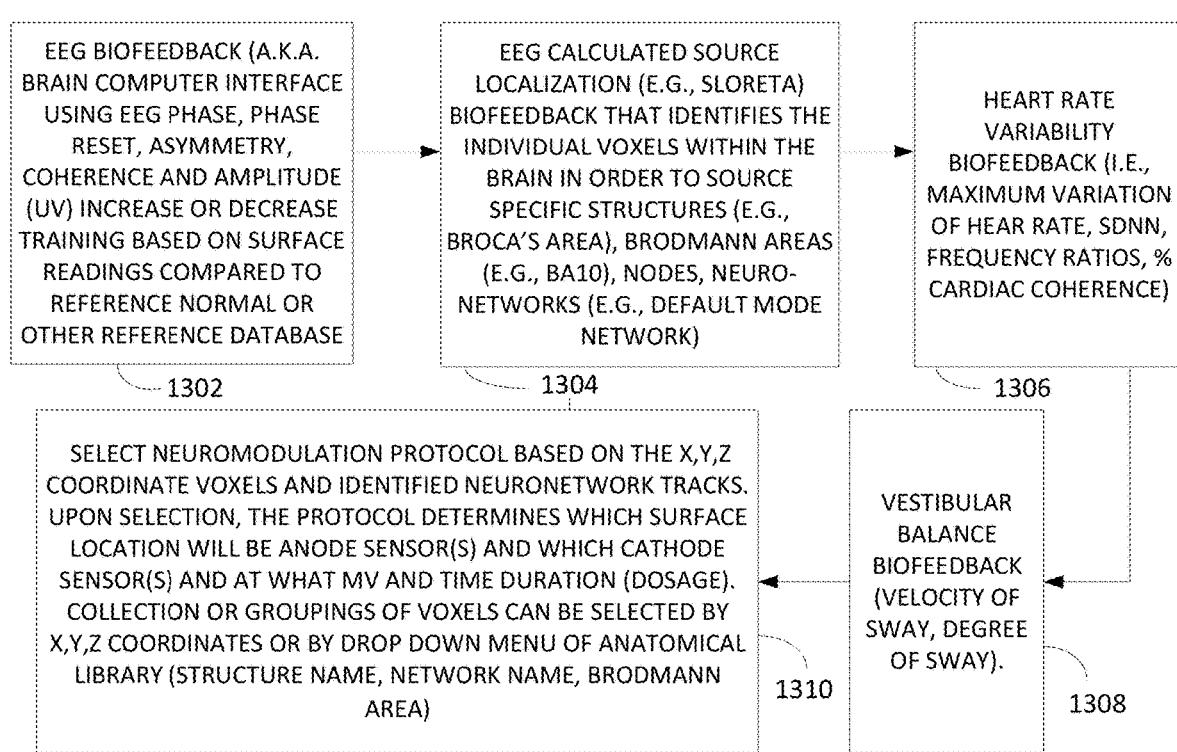
FIG. 13 illustrates a data flow diagram of one embodiment of calculating individualized intervention protocols phase of the clinical application process.

FIG. 13 illustrates steps relating to the calculation of individualized intervention protocols, Phase 906 of FIG. 9. Step 1302 is the EEG biofeedback, such as a brain computer interface using EEG Phase, Phase Reset, Asymmetry, Coherence and Amplitude (uV) increase or decrease training based on surface readings compared to reference normal or other reference database data.

Step 1304 is the EEG calculation source localization, e.g. sLORETA, biofeedback that identifies the individual voxels within the brain in order to source the specific structures, Brodmann areas, nodes, and/or neuro-networks.

Step 1306 is the determination of heart variability biofeedback, i.e. maximum variation of heart rate, SDNN, RMSSD, frequency ratios, percentage cardiac coherence.

This step may be performed by reading heart rate variability biofeedback information from the data acquisition described above.

Step 1308 is the determination of vestibular balance biofeedback, such as by way of example velocity of sway and degree of sway. Similar to step 1306, this data can be acquired based on the data acquisition techniques described above.

Step 1310 is the selection of neuromodulation protocols based on the x, y and z coordinate voxels and the identified neuronetwork tracks.

Upon selection, the protocol determines which surface location with be anode sensors(s) and which cathode sensor(s) and at what MV and time duration (e.g. dosage). In one embodiment, the collections or groupings of voxels can be selected by x, y, z coordinates or by drop down menu using an anatomical library (e.g. structure name, network name, Brodmann Area).

Measurements and quantification of the physiology (e.g., EEG, ECG, ERPs, balance) are obtained using sensor array and other electronic measurement components (i.e., gyroscope, accelerometer) and processed with algorithms for signal cleaning, artifact removal, and interpretive analysis against norm groups. Additional subjective data collected is computed for goodness-of-fit, such as noted below, to ensure ample overlap of objective and subjective data so that physiology findings is consistent with symptom complaints or peak performance objectives. Voxels, or clusters or neurons, are targeted using source localization x, y, z mathematics (i.e., sLORETA) and each voxel or mega-voxel (larger cluster of voxels) are calculated for normalcy against normal or special population databases for several functional measures to include 1 Hz bins frequency amplitude, coherence, phase, phase reset. Those voxels that fall outside of set normal limits or targeted peak performance limits (e.g., z-score+/−1.0) are listed for intervention targeting with combined or in isolation neuromodulation techniques to include pulsed or non-pulsed ultrasound neuromodulation, tDCS, tACS, magnetic field and brain computer interface, balance training, heart rate variability biofeedback, or other user defined and delivered interventions. Follow the intervention process a repeat assessment is calculated based on the differences across all physiology measures and differences across subject/patient self-report data submitted. The cycle can repeat until pre-selected normal or peak performance limits are achieved or the user choses to disconnect the cycle of measurement, modulate, train, re-measure.

Figure 14:
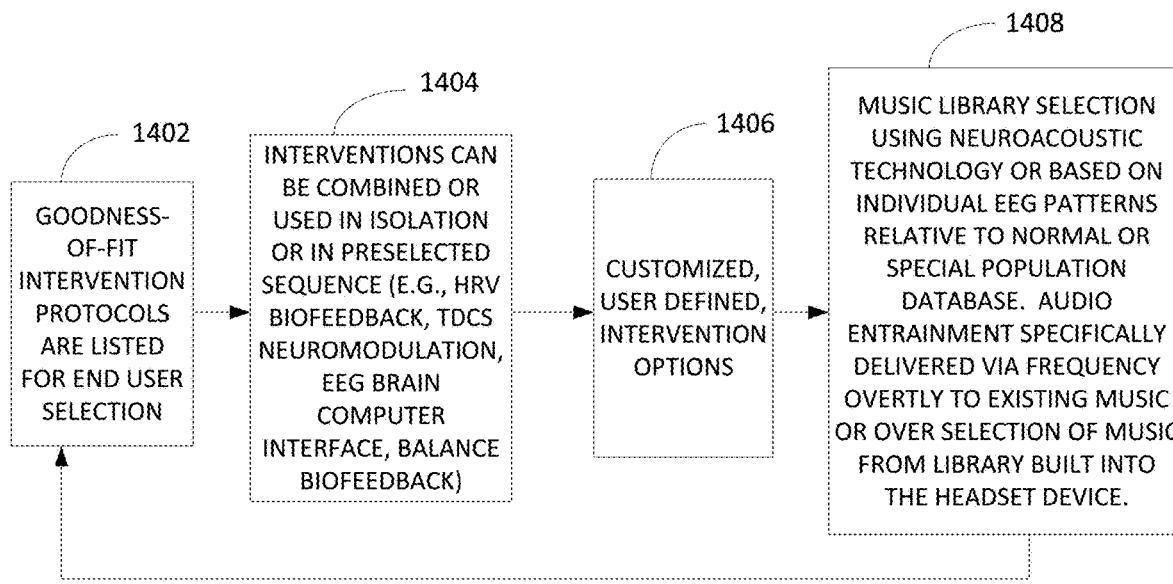
FIG. 14 illustrates a data flow diagram of one embodiment of a user selection or automated launch protocols phase of the clinical application process.

FIG. 14 illustrates steps of one embodiment of the user selected or automated launch protocols, phase 908 of FIG. 9. Step 1402 provides that goodness-of-fit intervention protocols are listed for end user selection.

Goodness-of-fit refers to overlapping physiology biomarkers (e.g., low 8-12 Hz EEB power in locations F3 relative to location F4; Brodmann Area 25 z-score greater than −1.5) known to correlated with subjective selection of symptoms or signs (e.g., lethargy, flat affect, insomnia) and additionally current diagnostic labels (e.g., Major Depression, Mild Cognitive Impairment). A correlational analysis of the available data both confirms the relationship between symptoms and biomarkers but also calculates a quantified degree of severity from a normal health sample group.

Step 1404 provides that interventions can be combined or used in isolation or in a preselected sequence. For example, a heart rate variability biofeedback, tDCS neuromodulation, EEG brain computer interface, balance biofeedback.

Step 1406 provides for any customized user defined intervention options. Step 1408 is the selection of a music library using neuroacoustic entrainment technology or based on individual EEG patterns relative to normal or special population database data. In one embodiment, audio entertainment may be specifically delivered via frequency tones or overtly to existing music or over selection of music from a library built into a headset device, such as the device of FIG. 8.

In one embodiment, the methodology of FIG. 14 therein reverts back to step 1402 for further modulation, adjustment, refinement or processing, if necessary.

Figure 15:
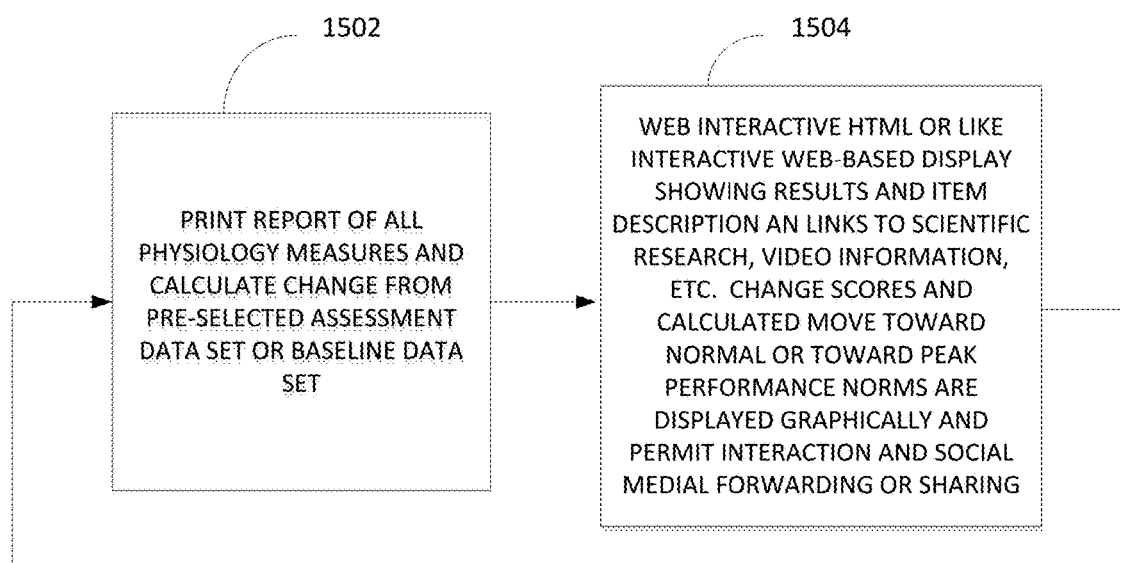
FIG. 15 illustrates a data flow diagram of the phase for calculating and displaying physiology changes of the clinical application process.

FIG. 15 illustrates steps of the phase for calculation and display of physiology change, phase 910 of FIG. 9. Step 1502 is the printed report of all physiology measures and calculated change from pre-selected assessment data set or baseline data set. In one embodiment, the report provides the deltas or changes in values over any number of selected intervals. For example, one embodiment can be changes over a full treatment period. In another example, the changes can be from a previous or prior treatment iteration. Moreover, the printed report may be modified or adjusted to customize for specific features or changes, as recognized by one skilled in the art.

Step 1504 is the generation of web interactive HTML or similar network-based interactive display showing results and item descriptions. The interactive display may include active links to associated content, such as scientific research, video data, etc. The display may additionally include graphical information plotting measured changes across time periods.

A further method for neuromodulation therapy includes the methods and systems described above, further including processing operations for detecting a brain malady of a patient. Existing medicinal solutions alone are limited in offering long-term symptom relief of brain maladies, for example neurodegenerative dementia conditions. Whereas non-invasive brain stimulation can offer relief to patients.

As used herein, a brain malady is any type of illness or other condition associated with the brain, including but not limited to dementia, depression, Alzheimer's, aphasia, mild brain injury, traumatic brain injury, etc. For example, front temporal dementia is a type of dementia where, when correctly diagnosed, responds well to non-invasive brain stimulation treatments. Effectiveness of these brain stimulation treatments are predicated in large part on proper detection of clear region(s) of interest within the brain and proper source localization of stimulation therapy. Incorporating neurostimulation with additional patient testing and feedback systems, improves the effectiveness of neurostimulation. Additional benefits can be found using imaging and other external factors, such as MRI readings and software analysis of MRI data, by of example.

The method includes processing operations, building upon the data collection noted above, for estimating a brain malady type and a severity value for a patient. As described herein, the further neuromodulation therapy includes machine learning/deep learning operations to generate reference data used to determine a patient's brain cognition status based on measurement data in relation to existing measurement data from varying sources.

The present method includes machine learning operations for generating and using data sets for estimating the brain malady within a specific category and the severity value providing a range or estimate of likeliness of said categorization.

Dementia includes loss of cognitive functions, a common example being Alzheimer's and its degenerative state(s).

Brain injuries can include mild traumatic brain injury (TBI) to severe brain injury, with stages therebetween.

The present methodology builds upon existing testing and data acquisition techniques to collect patient data, including the techniques noted above. Predictive accuracy with machine learning enhances the collection of multiple non-invasive electrophysiological measures. These measures can include quantitative electroencephalography (qEEG) values, such as but not limited to absolute and relative amplitude, coherence, time frequency analysis, spectral analysis, and dominant peak EEG rhythm. Additional measures include event related potentials (ERP) recorded at each electrode location following time locked delivery of differing visual and auditory stimulus types. These added ERP values can allow for including omission and commission error and response speed, which allows for adding performance values (e.g. body value measurements) to the electrical measurements of the brain under resting and test conditions.

Additive computerized neuropsychological test values of effort on standardized tests, for example MoCA, Symbol-Digit, Trails A and B, or blood and/or saliva values can also be body value measurements aiding in machine learning calculations. Another body value measurement can be a force plate measurement, e.g. block 226 of FIG. 2, and balance correction speeds.

Based on the processing algorithms, the present method therein generates a treatment protocol for treating or mitigating the brain malady. The treatment protocol includes transcranial stimulation, for example the stimulation devices noted in FIGS. 1 and 6 above.

Figure 16:
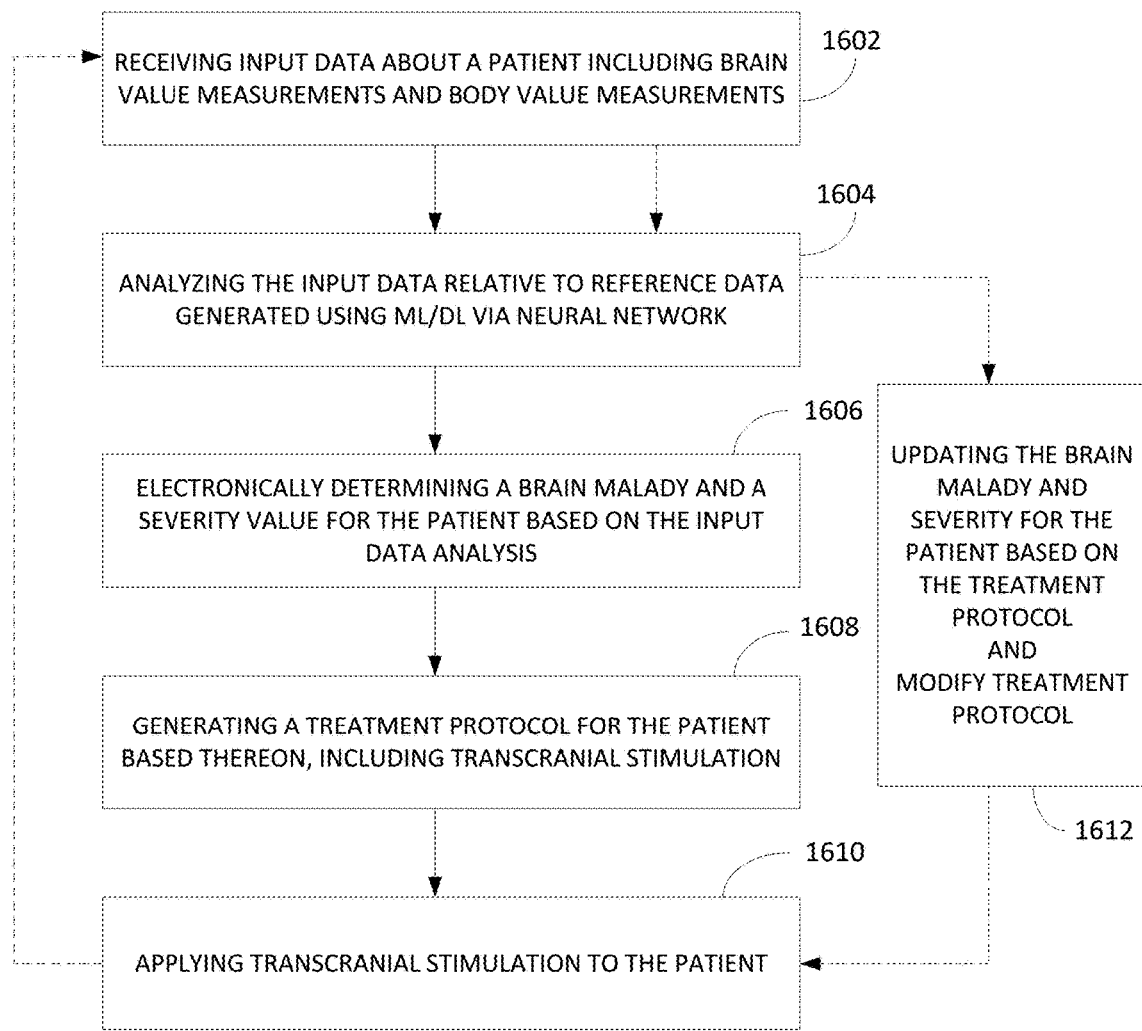
FIG. 16 illustrates a data flow diagram for a neuromodulation therapy.

FIG. 16 illustrates a flowchart of the steps of one embodiment of the neuromodulation therapy method. A first step, step 1602, is receiving input data about a patient including brain value measurements and body value measurements. As used herein, brain value measurements relate to values acquired using helmet or other transcranial stimulation device, such as device 100 of FIG. 100. The brain value measurements can additionally include external measurements values, such as measurements or data acquired from MRI or other scanning technology.

As used herein, body value measurements relate to any values associated with the patient not directly found within the brain value measurements. By way of example, body value measurements can include heart rate or EEG values acquired using electrodes or blood volume pulse sensors placed on the patient's skin. Another example of body value measurements can be balance plate measurements from a patient standing on a balance plate. Another example of body value measurements can be blood or tissue samples from the patient. The above examples are exemplary in nature and not an exclusive or exhaustive list of types of measurement values, whereby the body measurement values can include any additional values as recognized by one skilled in the art.

Acquisition of the brain value measurements and the body value measurements can be using techniques described above. For example, FIG. 2 above notes of generating and receiving non-invasive measurements (brain value measurements) of electrical currents in the brain of a patient. FIG. 2 also illustrates inclusion of sensory stimuli as secondary (body value) measurements.

In a further embodiment, these values can be imported or acquired from additional or third-party sources, for example receiving blood sample readings from a lab or downloading heart and cardiac rhythms from a fitness tracker or third-party application.

The measurements acquired from the patient can include measurements from one or more EEG electrodes on the patient's head and electrocardiograph electrodes on the chest and head and force plate movements under task and balance conditions. Values from these measurements can include, but are not limited to, qEEG amplitude, sensory and cognitive event related potentials, phase, network coherence, dominant peak EEG rhythm by brain region, frequency band statistics (i.e. alpha1:alpha2 ratio), current dipoles, source localization calculations (e.g. LORETA, LAURA), time-frequency analysis techniques (e.g. discrete and continuous wavelet transform, Fourier transform).

In the methodology of FIG. 16, step 1604 is electronically analyzing the input data relative to reference data, the reference data generated using machine learning and deep learning (ML/DL) operations. This reference data generation is described in a greater detail below. The analysis can include using decision tree nodes, the nodes generated based on the ML/DL operations.

Step 1606 is electronically determining a brain malady and a severity value for the patient. The brain malady, for example, can indicate the patient is likely to have a mild TBI with a severity value estimating the likelihood within a specific percentage range. This determining step is performed by at least one processing device using the patient data and referencing the reference databases.

As described in further detail below, step 1606 can include generating values predicting a cognitive category, also referred to as the brain malady, with a diagnostic accuracy, also referred to as the severity value. In one embodiment, the cognitive category can include three categories: dementia (AD), mild cognitive impairment (MCI), and subjective cognitive impairment (SCI). It is recognized that further categories as recognized by one skilled in the art are within the scope of the present disclosure.

In one embodiment, a computation value for the cognitive category with diagnostic accuracy can be expressed as an area under a curve (AUC). For example, in one embodiment, the predictive cognitive category of persons with a diagnostic accuracy of 0.79 can be shown relative to:

AUC=0.96 (95% CI), between AD and SCI.
AUC=0.89 (95% CI), between AD and MCI.
AUC=0.92 (95% CI), between MCI and SCI.

Based thereon, step 1608 is generating a treatment protocol for the patient based at least on the brain value measurements, the brain malady, and the severity value. The treatment protocol includes parameters for transcranial stimulation using an EEG, including for example TMS or any other suitable type of stimulation. The treatment protocol further includes voltage strength and duration values, as well as location instructions for where to apply stimulation to the head of the patient.

In one embodiment, the generation of the treatment protocol can include using a look-up table or other reference table having recommended treatment protocols relative to the brain malady and related data. The treatment protocol includes transcranial stimulation parameters usable for step 1610 below. These parameters can include current levels and duration instructions for transcranial sensors, as well as sensor placement instructions.

Therefore, step 1610 is applying the transcranial stimulation to the patient consistent with the treatment protocol. Accordingly, the patient is the given a personalized treatment protocol in accordance with the patient's brain malady, for example a specific type of depression is treated with a designated tES protocol.

The present method includes transcranial stimulation via at least one anode and at least one cathode electrode to the brain of the patient. The method augments this non-invasive stimulation based on the brain malady and severity value using, in one embodiment, a region of interest hierarchy. Herein, the regions of interest of the patient's brain are presented in x-y-z coordinates of the brain based the patient's head measurements and in relation to best fit automated stereotaxis coordinate atlas library or multiple libraries that include but are not limited to Talairach, Tournouz, and Montreal Neurological Institute. The patient brain source imaging locations can also account for minimal norm solution and weight minimum norm solution (e.g. LORETA, LAURA). Herein, the operations may utilize similar techniques noted above in step 1206 of FIG. 12.

Application of the transcranial stimulation may be similar to step 240 of FIG. 2, herein using the treatment protocol accounting for the dementia type and severity value for the patient.

The present method can additionally iterate for on-going treatments. Another embodiment can include the method reverting to step 1602 for additional data gathering after (or during) the treatment protocol. As noted by the dashed line, this iterative process can then proceed again to step 1604 to further analyze the input data. Herein, step 1612 provides for updating the brain malady and severity value for the patient relative to the initial treatment protocol. Based thereon, step 1612 may include modifying the treatment protocol as needed and proceeding to step 1610 for further application of the neuromodulation stimulation.

In one example, a patient may receive a clinical diagnosis of depression. The patient dons the EEG headset, e.g. FIG. 1, and the headset collects electrophysiology raw data. This data may be in analog format, subject to conversion to digital format. The patient is also subject to additional testing, such as an EKG, balance plate, or other testing protocols as noted above. This also collects further data.

The processing of the headset data (brain value measurements) and body value measurements can produce a report for the patient's doctor. The data analysis includes the dementia type, which in this example can indicate a subtype depression with an underactive left front brain region and the right front brain region being overactive. Based thereon, the electronically generated treatment protocol for the patient could, in this embodiment, direct neuromodulation to increase activity of the neurons on the frontal left and inhibit over activity of the front right region. Tracking the treatment protocol can further include specificity or sensitivity to relate different types of brain maladies, for example specific type of depression, e.g. atypical or mixed depression.

Figure 17:
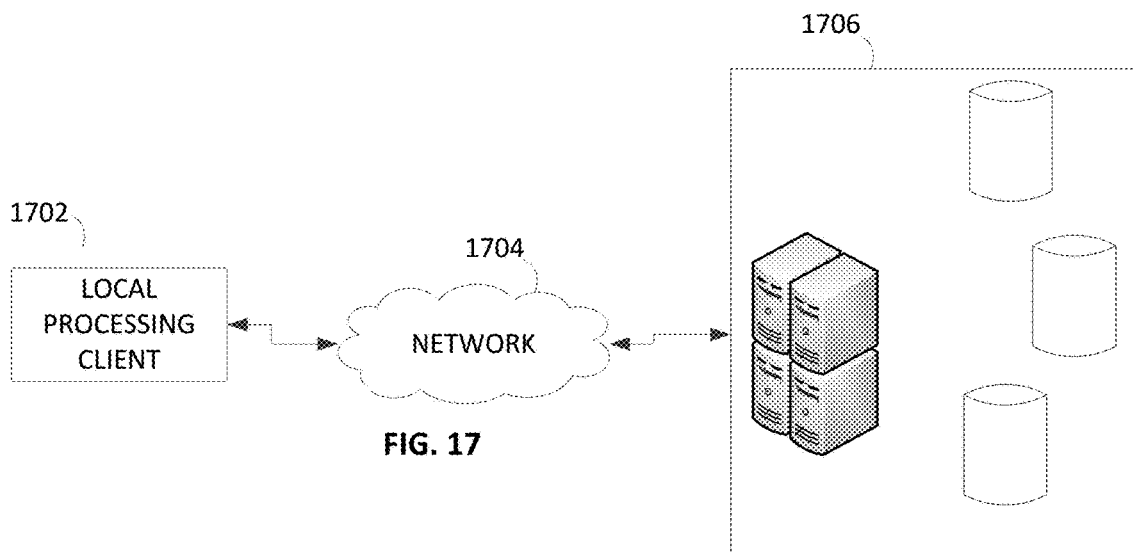
FIG. 17 illustrates a computing environment including machine learning operations for brain disease detection and assessment as part of the neuromodulation therapy.

FIG. 17 illustrates one embodiment of the processing environment for the ML/DL operations. The processing environment includes a local processing client 1702, such as allowing for a clinician or other user to enter patient data. This local client 1702 can also include automated data gathering operations, such as being connected to an EEG and other data collection devices.

One embodiment includes a local executable collecting data, either via data entry or via data capture, encapsulating the data into a usable format, and transmitting the data to a server 1706 or other network processing device via a network 1704. The server 1706 can be any number of processing devices allowing for machine language and artificial intelligence processing operations, such as in a cloud computing environment. The server 1706 further includes access to any number of reference databases usable to best-fit analysis or supplementing the machine learning operations.

The network 1704 can be any suitable network, such as a private or public network, for example the Internet. Transmission of data can include encryption and other techniques for masking or otherwise maintain patient confidentiality.

Figure 18:
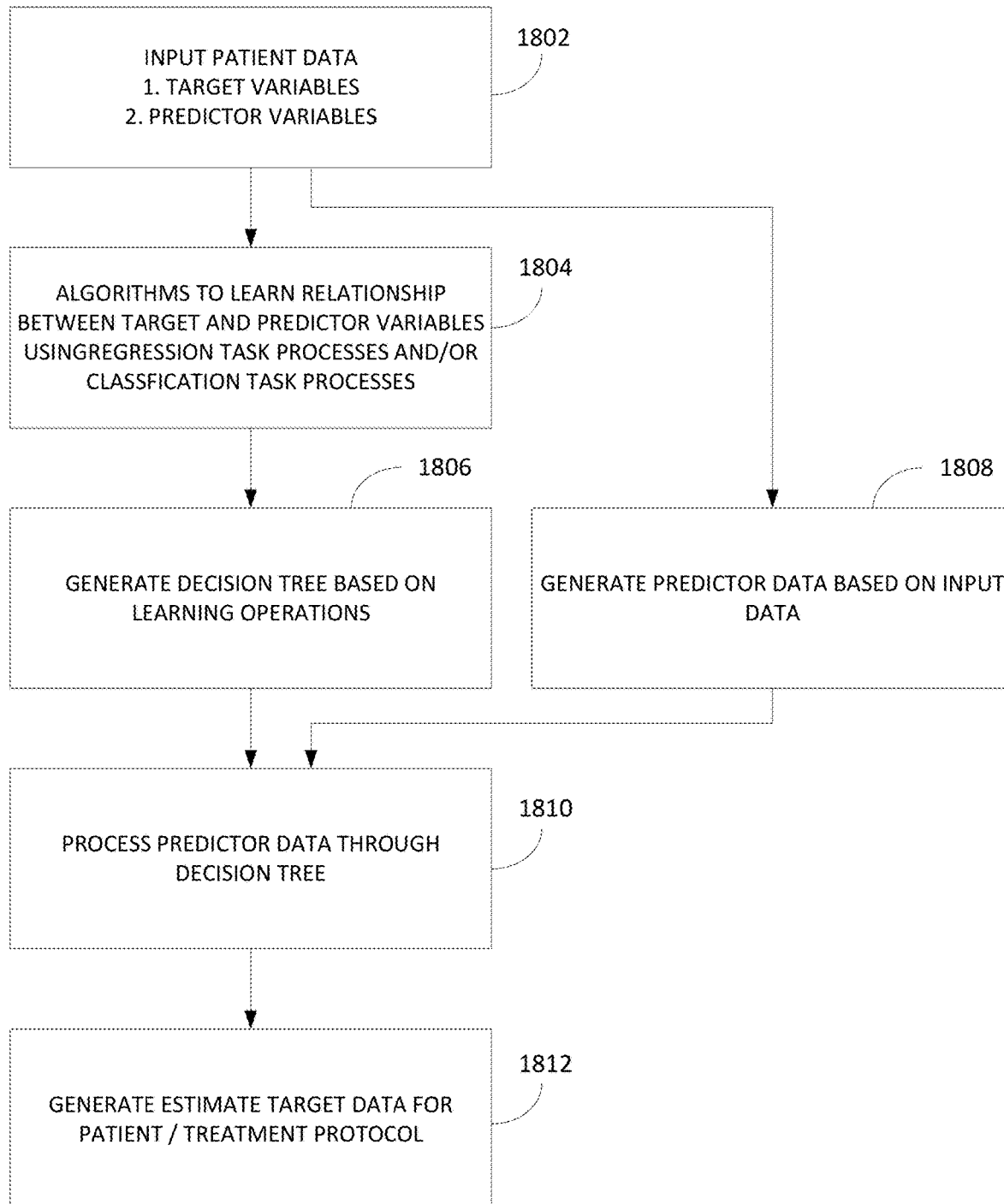
FIG. 18 illustrates a data flow diagram of one embodiment of the electronic analysis of patient input data for the neuromodulation therapy.

The server 1706 performs processing operations as noted herein, including as described in greater detail in FIG. 18. Therein, the processing operations generate the brain malady and severity value for the patient, as well as the treatment protocol based thereon. These values and the treatment protocol can then be transmitted back to the local client 1702 via the network 1704.

At the local client 1704, a clinician or other user can then provide transcranial stimulation to the patient consistent with the treatment protocol. In one embodiment, the treatment protocol can be manually set by the clinician. In another embodiment, a further executable software module may then translate the treatment protocol into neuromodulation instructions for the transcranial stimulation treatment given to the patient.

In one example, the patient may have the transcranial stimulation device placed on his or her head. The local client 1702 then runs the treatment protocol by applying transcranial stimulation at different nodes on the patient.

The above described method and processing system uses ML/DL operations for improving patient diagnosis and efficacy of treatment with tailored treatment protocols. FIG. 18 illustrates the two-part process, with a first part being the ML/DL training to generate the reference data and the second part utilizing the decision tree generated by the first part training.

Step 1802 is collection of input patient data. As described in detail above, this patient data includes target variables and predictor variables. The target variables can be clinical data associated with the patient, predictor variables can be measured variables predictive for the patient, for example EEG derived quantities.

Step 1804, the ML/DL executable applications learn relationships between target and predictor variables using regression task processes and/or classification task processes.

The machine learning model consumes multiple electrophysiology and laboratory values (for example peak amplitude of alpha at location from Pz, O1, Oz, O2, blood homocysteine, APOE4, hA1C) that predict the dementia subtype and severity of a patient. The degree of sensitivity and specificity varies depending on the number of input values. The machine learning operations refines the learning models based on continuous quantification of values. For example, even patients that fall within a healthy category may be ranked with risk factors (e.g., two copies of APOE4, low parietal peak alpha, delayed P300b). These operations may additionally be performed or expanded using deep learning processing techniques.

In one example of ML/DL processing, the present system can build upon existing relationships between varying data sets associated with previously-diagnosed patients. For example, one data analysis and learning technique can use time frequency analysis and strengths of oscillations at different frequencies over time acquired using an EEG headpiece. In one example, a healthy patient can exhibit a dominant alpha at 10 Hz, but this is not found with Alzheimer patients. One data analysis technique may include taking alpha wave frequency images, converting them to grayscale, entering them into a computer vision model called a convolutional neural network, and let the neural net discover the patterns that differentiate healthy people from Alzheimer's patients.

Another machine learning operation includes generating a confusion matrix showing classifier performance. One technique includes a leave-one-out approach, training the model on all but one subject and then predict the label for the one held out subject. This technique includes repeating the procedure until each subject was the one held out. Therein, the matrix is the tally of those predictions. These operations may additionally be performed or expanded using deep learning processing techniques.

Another data collection and analysis technique can include statistics that include t-score values for the patient relative to known healthy values. This can include capturing EEG frequency band (i.e. alpha, theta, beta, gamma) power values for various regions of the patient's brain using specific sensors of the EEG headpiece. The difference in values and mapping of the values to specific regions is usable for predicting brain disease.

The ML/DL computations and learning are based on available data inputs, for example EEG data, ERPs, ECG, vestibular balance values, symptom values, behavioral performance values. The ML/DL computations process these input values to detect not only goodness of fit to diagnosis but more importantly the better goodness of fit for particular non-invasive tES operations and protocols. tES can include, but is not limited to, tDCS, tACS, TBS, rTMS, ultrasound pulse stimulation.

In one example a 1 Hz left frontal rTMS may be shown to be likely effective compared to 10 Hz rTMS or to TBS. The ML/DL computations guide goodness of fit of the brain malady with a more likely transcranial stimulation intervention option.

In one embodiment, the ML/DL operations are performed using a neural network model. In one embodiment, a deep network can include 4 layers with multiple nodes per layer. The specific data sets per node can be adjusted consistent with machine learning and deep learning operations.

In this exemplary embodiment using four layers, the first layer can include 15 nodes using tan h activation for data analysis. A second layer can include five nodes, also using tan h activation. A third layer includes three nodes and a output layer includes three nodes. In this exemplary deep network, the nodes facilitate fitting the input data to a corresponding output of a decision tree or other reference database usable for determining a brain malady and severity value.

The layers and nodes per layer seek to generate determined results based on the data. For example, can the data differentiate if the patient is male or female with an at least 98% accuracy? The node processing the data meets defined standards of data analysis with a result accuracy or reliability. For example, a node can determine with a high accuracy the gender of the patient. A next level or node can determine within an accuracy level if the patient is depressed or not-depressed based on input data. A third level or node can be if the patient satisfies conditions for an Alzheimer's diagnosis, with a secondary inquiry of level or type of diagnosis.

The machine learning operations of step 1804 can use any suitable data for predictive learning benefits. Therefrom, based on machine learning operations, step 1806 is generating a decision tree based thereon. The decision tree can be a node-based decision model or any other suitable referencing module for predictive values.

In one example, the decision tree can include step-wise decision operations for analyzing the patient data. Steps 1802-1806 are for building and re-iterating the decision tree. Steps 1802-1806 can be iterative, updating and refining the machine learning as additional source data (patient and/or reference data) becomes available.

The input patient data is additionally usable for predicting a dementia type for the patient. In step 1808, the patient data is processed to generate predictor data. As discussed above, there can a large amount of patient data available, whereby the using of this patient data can be directed to specific values or a grouping of values, or even an iterative process. For example, brain value measurements can be a first level analysis with body value measurements for refining the analysis. In another example, brain value measurements and selected body value measurements are initially analyzed with additional measurements (other brain value and/or body value) used for additional refinement.

Step 1810 is processing the patient data using the decision tree to generate the predictor data. Step 1808 and step 1810 can be an iterative process or a single data call operations.

Step 1812 is generating the estimate target data for the patient and a treatment protocol. Using the embodiments above, this estimate target data can be a clinical diagnosis value relating to brain disease, such as the being categorized as pathology types that include AD, MCI, SCI, front temporal dementia, DLB, and depression. This value is the brain malady, e.g. a dementia or depression type, and includes a severity value indicating a likelihood or reliability value associated with the brain malady assessment.

Therein, based on the dementia type, step 1812 includes generating a treatment protocol. One technique can be a look-up table or other reference database using known treatment protocols for specific dementia types.

The treatment protocol can also be modified based on any other suitable or available data, including the brain value measurements and body value measurements. For example, if a subtype of dementia is estimated based on a underdeveloped brain region, the treatment protocol may be modified to account for this brain value measurement. The treatment protocol may also include adjustments, modifications, or supplementation by a medical profession.

In one exemplary embodiment, a patient is subjected to multiple electroencephalogram sensor placement on the scalp and electrocardiogram sensors on the body for collective EEG recordings, event related potential recordings (e.g., P300a, P300b, N100, P200). These are in addition to vestibular balance testing, neuropsychological tests, blood tests, genetic testing with saliva, presenting symptoms, and individual demographics. These recordings are processed for artifact correction and statistical values that include z-score, t-score, and measures of difference from database reference groups (e.g., Alzheimer's disease, Bipolar Depression, Aphasia, Mild Cognitive Impairment, Normal, and Athlete Peak Performance).

Machine learning and deep learning calculations are applied to all the input values that systematically differentiate and generate brain malady typology and severity predictions. These machine learning predictions render sensitivity and specificity values against the library of comparison reference groups and matching to brain malady goodness of fit to particular disease endophenotypes.

By machine learning isolation of these brain malady subtypes, predictive values determine improved treatment intervention protocols. For example, in the case of a left frontal brain region hypofunction in the alpha frequency band, the intervention selection would list three neuromodulation clinical options, those being (a) rTMS 10 Hz at location F3, (b) brain computer interface enhance 8-10 Hz power at location F7 and F3 with suppression of slow content power 3-7 Hz, and (c) tDCS anode at F7 and cathode at Fp2 for 15 minutes of 1.5 mA direct current.

Following the matched treatment intervention, the recording of some number of repeated values (EEG, ERPs and ECG) are post processed and secondly input into the comparison statistical analysis and machine learning methods to generate measured improvements of the pre-treatment brain malady condition. Secondarily, the predictive positive response to individualized treatment type strengthens the brain malady subtyping prediction. The machine learning accounts for all input values and determines which minimal number of values (e.g., peak alpha, elevated frontal theta EEG frequency dominance, SDNN, reaction time) still offer high predictive value, or the minimal number of test values that still highly predicts the brain malady and associated matching effective treatment option.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods, systems, and devices described hereinabove are also contemplated and within the scope of the disclosed technology.

What is claimed is:

1. A neuromodulation therapy method comprising:
   receiving brain value measurements and body value measurements relating to a patient;
   electronically analyzing the brain value measurements and body value measurements relative to reference data generated based on machine learning operations associated with existing patient data and reference database data;
   based thereon, electronically determining, using at least one processing device, a brain malady and a severity value, for the patient; and
   electronically generating a treatment protocol for the patient based at least on the brain malady and the severity value, wherein the treatment protocol includes a voltage strength level, a duration, and position factors for transcranial sensors providing neurostimulation to the patient.

2. The method of claim 1 further comprising:
   applying a transcranial stimulation to the patient based on the treatment protocol.

3. The method of claim 2 further comprising:
   after applying the transcranial stimulation to the patient, acquiring secondary brain value measurements and secondary body value measurements;
   electronically analyzing the secondary brain value measurements and secondary body value measurements in reference to the reference data; and
   electronically determining a change value for the patient relative to the brain malady and severity value.

4. The method of claim 3 further comprising:
   generating an updated treatment protocol for the patient based on the electronic analysis of the secondary brain value measurements and secondary body value measurements.

5. The method of claim 1 further comprising:
   the brain value measurements include first electrophysiological values obtained from a brain of the patient using at least one EEG electrode; and
   the body value measurements include second electrophysiological values obtained from the patient including at least one of: an electrocardiograph electrode connected to the patient and force plate measurements measuring task and balance conditions of the patient.

6. The method of claim 1, wherein the brain malady includes at least one of: Alzheimer's, dementia, depression, mild cognitive impairment, and subjective cognitive impairment.

7. The method of claim 6, wherein the severity value assesses an accuracy level of the brain malady of the patient.

8. The method of claim 1, wherein the body value measurements include at least one of: a blood content value and a brain processing speed value.

9. The method of claim 1, wherein the electronic analysis of the brain value measurements and the body value measurements includes using source localization models to isolate voxels within a brain of the patient to detect at least one region of the brain of the patient affected by the brain malady.

10. The method of claim 9, wherein the electronic analysis includes referencing at least one brain mapping library.

11. The method of claim 1, wherein the reference data is generated based on machine learning processing operations and deep learning processing operations executed within at least one neural network.

12. A neuromodulation therapy method comprising:
    receiving brain value measurements and body value measurements relating to a patient;
    electronically analyzing the brain value measurements and body value measurements relative to reference data generated based on machine learning operations associated with existing patient data and reference database data;
    based thereon, electronically determining, using at least one processing device, a brain malady and a severity value, for the patient;
    electronically generating a treatment protocol for the patient based at least on the brain malady and the severity value,
    applying a transcranial stimulation to the patient based on the treatment protocol;
    after applying the transcranial stimulation to the patient, acquiring secondary brain value measurements and secondary body value measurements;
    electronically analyzing the secondary brain value measurements and secondary body value measurements in reference to the reference data; and
    electronically determining a change value for the patient relative to the brain malady and severity value.

13. The method of claim 12, wherein the treatment protocol includes a voltage strength level, a duration, and position factors for transcranial sensors providing neurostimulation to the patient.

14. The method of claim 12 further comprising:
    generating an updated treatment protocol for the patient based on the electronic analysis of the secondary brain value measurements and secondary body value measurements.

15. The method of claim 12 further comprising:
    the brain value measurements include first electrophysiological values obtained from a brain of the patient using at least one EEG electrode; and
    the body value measurements include second electrophysiological values obtained from the patient including at least one of: an electrocardiograph electrode connected to the patient and force plate measurements measuring task and balance conditions of the patient.

16. The method of claim 12, wherein the brain malady includes at least one of: Alzheimer's, dementia, depression, mild cognitive impairment, and subjective cognitive impairment.

17. The method of claim 12, wherein the severity value assesses an accuracy level of the brain malady of the patient.

18. The method of claim 12, wherein the body value measurements include at least one of: a blood content value and a brain processing speed value.

19. The method of claim 12, wherein the electronic analysis of the brain value measurements and the body value measurements includes using source localization models to isolate voxels within a brain of the patient to detect at least one region of the brain of the patient affected by the brain malady.

* * * * *